US012139507B2

(12) United States Patent
Kataoka

(10) Patent No.: US 12,139,507 B2
(45) Date of Patent: Nov. 12, 2024

(54) SEGMENT FOR USE IN SYNTHESIS OF OLIGONUCLEOTIDE, METHOD FOR PRODUCING THE SAME, AND METHOD FOR SYNTHESIZING OLIGONUCLEOTIDE USING THE SAME

(71) Applicant: NATiAS Inc., Hyogo (JP)

(72) Inventor: Masanori Kataoka, Hyogo (JP)

(73) Assignee: NATiAS Inc., Hyogo (JP)

( * ) Notice: Subject to any disclaimer, the term of this patent is extended or adjusted under 35 U.S.C. 154(b) by 1015 days.

(21) Appl. No.: 17/051,931

(22) PCT Filed: May 7, 2019

(86) PCT No.: PCT/JP2019/018299
§ 371 (c)(1),
(2) Date: Oct. 30, 2020

(87) PCT Pub. No.: WO2019/212061
PCT Pub. Date: Nov. 7, 2019

(65) Prior Publication Data
US 2021/0269470 A1 Sep. 2, 2021

(30) Foreign Application Priority Data

May 2, 2018 (JP) ................................. 2018-088912

(51) Int. Cl.
*C07H 21/02* (2006.01)
(52) U.S. Cl.
CPC .................................... *C07H 21/02* (2013.01)
(58) Field of Classification Search
None
See application file for complete search history.

(56) References Cited

U.S. PATENT DOCUMENTS

| | | | |
|---|---|---|---|
| 5,717,085 A | | 2/1998 | Lyttle et al. |
| 5,869,644 A | * | 2/1999 | Shortle ................. C12N 15/102 536/25.3 |
| 6,294,664 B1 | | 9/2001 | Ravikumar et al. |
| 2010/0273999 A1 | | 10/2010 | Jung |
| 2013/0184450 A1 | | 7/2013 | Wada et al. |
| 2014/0256926 A1 | * | 9/2014 | Damha ................. C07D 233/60 558/275 |
| 2018/0291056 A1 | | 10/2018 | Yamashita et al. |
| 2021/0317158 A1 | | 10/2021 | Kataoka |
| 2022/0235089 A1 | | 7/2022 | Kataoka et al. |

FOREIGN PATENT DOCUMENTS

| | | |
|---|---|---|
| JP | 62070392 A | 3/1987 |
| JP | H08502642 | 3/1993 |
| JP | H1072448 A | 3/1998 |
| JP | 2006248949 A | 9/2006 |
| WO | WO 93/21203 | 10/1993 |
| WO | WO 96/16073 | 5/1996 |
| WO | WO 2011/061115 A1 | 5/2011 |
| WO | WO 2011/108682 A1 | 9/2011 |
| WO | WO 2012/024776 A1 | 3/2012 |
| WO | WO 2017/111137 A1 | 6/2017 |
| WO | WO 2019/212061 | 7/2019 |
| WO | WO 2019/212063 | 7/2019 |

OTHER PUBLICATIONS

Virnekäs, Bernhard, et al. "Trinucleotide phosphoramidites: ideal reagents for the synthesis of mixed oligonucleotides for random mutagenesis." Nucleic acids research 22.25 (1994): 5600.*
Roy, Subhadeep, and Marvin Caruthers. "Synthesis of DNA/RNA and their analogs via phosphoramidite and H-phosphonate chemistries." Molecules 18.11 (2013): 14268-14284.*
Bonora, Gian Maria, et al. "Large scale, liquid phase synthesis of oligonucleotides by the phosphoramidite approach." Nucleic acids research 21.5 (1993): 1213-1217.*
Hayakawa et al. J. Am. Chem. Soc. (1997), vol. 119, pp. 11758-11762.*
Assessment Report, Spinraza, EMA/289068/2017, European Medicines Agency, Science Medicines Health, Apr. 21, 2017.
Caruthers, M.H., et al., "Synthesis of Oligonucleotides Using The Phosphoramidite Method," Proceedings of the 2$^{nd}$ International Symposium on Phosphorus Chemistry Directed Towards Biology, Held in Lods, Poland Sep. 8-12, 1986, pp. 3-21.
Chen, C.H., eta l., "Convergent Solution Phase Synthesis of Chimeric Oligonucleotides by a 2+2 and 3+3 Phosphoramidite Strategy", Aust. J. Chem, 2010, 63, 227-235.
Gaytán, P., et al., "TrimerDimer: an oligonucleotide-based saturation mutagenesis approach that removes redundant and stop codons", Nucleic Acids Research, 2008, 37(18) e125, 13 pages.
Guo, J., et al., "Solid-Phase Stereoselective Synthesis of 2'-O-Methyl-Oligoribonucleoside Phosphorothioates Using Nucleoside Bicyclic Oxazaphospholidines", Biorganic * Medicinal Chemistry Letters 8 (1998) 2539-2544.
Hassler, M., et al., "RNA synthesis via dimer and trimer phosphoramidite block coupling", Tetrahedron Letters 52 (2011) 2575-2578.
Hyodo, M., et al., "Utility of Azolium Triflates as Promoters for the Condensation of a Nucleoside Phosphoramidite and a Nucleoside in the Agrawal's Stereoselective Synthesis of Nucleoside Phosphorothioates", Eur. J. Org. Chem., 2005, 5216-5223.

(Continued)

*Primary Examiner* — Patrick T Lewis
(74) *Attorney, Agent, or Firm* — Hamilton, Brook, Smith & Reynolds, P.C.

(57) ABSTRACT

A segment for use in synthesis of an oligonucleotide, represented by the following formula (I), a method for producing the same, and a method for synthesizing an oligonucleotide therefrom are provided. In formula (I), B is a protected/unprotected nucleoside base; $R^1$ is a protecting group; $R^2$, $R^3$ and $R^4$ are $OCH_2CH_2CN$, $OCH_2CH=CH_2$, etc.; $R^5$ is a substituted/unsubstituted aliphatic group/aromatic group; X is a lone pair, O or S; Y is $NHR^6$, a halogen, CN, etc., or a hydroxyl group protected with an acyl, ether or silyl protecting group; $R^6$ is H, an aliphatic group or an aromatic group; Z is H, an alkyl, an O- or N-alkyl or a halogen, or forms a Z-Y bond with Y; and (m+n) is an integer of 2 or more and 23 or less.

10 Claims, 3 Drawing Sheets

(56) References Cited

OTHER PUBLICATIONS

International Search Report for International Application No. PCT/JP2019/018307, "Optically Active Segment for Stereocontrolled Oligonucleotide Synthesis, Production Method for Same, and Stereocontrolled Oligonucleotide Synthesis Method Using Same", dated Aug. 6, 2019.
Written Opinion for International Application No. PCT/JP2019/018307, "Optically Active Segment for Stereocontrolled Oligonucleotide Synthesis, Production Method for Same, and Stereocontrolled Oligonucleotide Synthesis Method Using Same", dated Aug. 6, 2019.
International Preliminary Report on Patentability for International Application No. PCT/JP2019/018307, "Optically Active Segment for Stereocontrolled Oligonucleotide Synthesis, Production Method for Same, and Stereocontrolled Oligonucleotide Synthesis Method Using Same", dated Nov. 3, 2020.
International Search Report for International Application No. PCT/JP2019/018299, "Segment for Oligonucleotide Synthesis, Production Method for Same, and Oligonucleotide Synthesis Method Using Same", dated Aug. 13, 2019.
Written Opinion for International Application No. PCT/JP2019/018299, "Segment for Oligonucleotide Synthesis, Production Method for Same, and Oligonucleotide Synthesis Method Using Same", dated Aug. 13, 2019.
International Preliminary Report on Patentability for International Application No. PCT/JP2019/018299, "Segment for Oligonucleotide Synthesis, Production Method for Same, and Oligonucleotide Synthesis Method Using Same", dated Nov. 3, 2020.
Janczyk et al., "A new and convenient approach for the preparation of β-cyanoethyl protected trinucleotide phosphoramidites," Organic & Biomolecular Chemistry, 2012, 10, 1510-1513.
Lyttle et al., "Mutagenesis Using Trinucleotide β-Cyanoethyl Phosphoramidites," Research Reports, BioTechniques, vol. 19, No. 2 (1995), 274-280.
Nukaga, Y., et al., "Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method", J. Org. Chem, 2016, 81, 2753.2762.
Oka, N., et al., "Solid-Phase Synthesis of Stereoregular Oligodeoxyribonucleoside Phosphorothioates Using Bicycle Oxazaphospholidine Derivatives as Monomer Units", J. Am. Chem. Soc., 2008, 130, 16031-16037.
Oka, N., et al., "Stereocontrolled synthesis of dinucleoside phosphorothioates using a fluorous tag", Journal of Fluorine Chemistry 150 (2013) 85-91.
Virnekäs, B., et al., Trinucleotide phosphoramidites: ideal reagents for the synthesis of mixed oligonucleotides for random mutagenesis, Nucleic Acids Research, 1994, 22(25).
Non Final Office Action for U.S. Appl. No. 17/051,936, "Optically Active Segment for Use in Synthesis of Stereocontrolled Oligonucleotide, Method for Producing the Same, and Method for Synthesizing Stereocontrolled Oligonucleotide Using the Same" dated Feb. 13, 2023.
Final Office Action for U.S. Appl. No. 17/051,936, "Optically Active Segment for Use in Synthesis of Stereocontrolled Oligonucleotide, Method for Producing the Same, and Method for Synthesizing Stereocontrolled Oligonucleotide Using the Same" dated Aug. 22, 2022.
Sekine, et al., Genome Chemistry, Apr. 10, 2003, 1-6 Pages, with Translation of relevant portion of reference and translation of JP Office Action from corresponding Japanese Application No. 2022-023844, "Oligonucleotide synthesis a segment and its manufacturing method, as well as methods for synthesis of oligonucleotides using the same", dated Jul. 11, 2023.
Final Office Action for U.S. Appl. No. 17/051,936, "Optically Active Segment for Use in Synthesis of Stereocontrolled Oligonucleotide, Method for Producing the Same, and Method for Synthesizing Stereocontrolled Oligonucleotide Using the Same" dated Aug. 7, 2023.
Hayakawa, Y., et al., "A Strategy for the Stereoselective Preparation of Thymididine Phosphorothioates with the® or the (S) Configuration at the Stereogenic Phosphorus Atom and Their Application to the Synthesis of Oligodeoxyribonucleotides with Stereochemically PUre Phosphate/Phosphorothioate Chimeric Backbones", Eur. J. Org. Chem. 2006, 3834-3844.
Office Action for U.S. Appl. No. 17/051,936, "Optically Active Segment for Use in Synthesis of Stereocontrolled Oligonucleotide, Method for Producing the Same, and Method for Synthesizing Stereocontrolled Oligonucleotide Using the Same" dated Apr. 8, 2022.
Non-Final Office Action for U.S. Appl. No. 17/051,936, "Optically Active Segment for Use in Synthesis of Stereocontrolled Oligonucleotide, Method for Producing the Same, and Method for Synthesizing Stereocontrolled Oligonucleotide Using the Same" dated Nov. 17, 2023.

* cited by examiner

SEGMENT FOR USE IN SYNTHESIS OF OLIGONUCLEOTIDE, METHOD FOR PRODUCING THE SAME, AND METHOD FOR SYNTHESIZING OLIGONUCLEOTIDE USING THE SAME

This application is the U.S. National Stage of International Application No. PCT/JP2019/018299, filed May 7, 2019, which designates the U.S., published in Japanese and claims priority under 35 U.S.C. § 119 or 365(c) to JP Application No. 2018-088912, filed May 2, 2018. The entire teachings of the above applications are incorporated herein by reference.

TECHNICAL FIELD

The present invention relates to a segment for use in synthesis of an oligonucleotide, a method for producing the same, and a method for synthesizing an oligonucleotide using the same.

BACKGROUND ART

In recent years, attention has been focused on nucleic acid drugs having a natural or non-natural oligonucleotide as basic skeleton. Production methods by chemical synthesis are widely used to obtain nucleic acid drugs designed to obtain an intended effect.

In oligonucleotide synthesis by conventional methods, using a monomer amidite as raw material, a method of extending the length of a nucleotide through a coupling reaction for each base step by step is mainly used (refer to Non-Patent Literature 1). The extension of bases one by one in the oligonucleotide synthesis requires a coupling reaction between a monomer amidite and the 5'-hydroxyl group of a nucleoside, and in addition to that, a step of oxidizing or sulfurizing phosphite and a step of deprotecting the protecting group for the 5'-hydroxyl group of the nucleoside in preparation for a subsequent coupling reaction.

CITATION LIST

Non Patent Literature

[NPL 1]
Caruthers et al., Bioactive Molecules, 3, pp. 3 to 21 (1987)

SUMMARY OF INVENTION

Technical Problem

In the case of using the raw material used in conventional method, however, the yield of each of the coupling reactions in the oligonucleotide synthesis does not necessarily reach 100%. For this reason, it is difficult to synthesize an oligonucleotide having a certain level of length at high efficiency.

An oxidation/sulfurization step and a deprotection step following the coupling reaction also do not always proceed at 100%. For this reason, the yield of the oligonucleotide having a target length decreases as the length of the target oligonucleotide increases.

Further, at the stage of finally obtaining an oligonucleotide having a target length, it is necessary to perform a purification step for removing by-products generated in each step as described above and reagent residues. Examples of the typical by-products generated in the method for synthesizing an oligonucleotide N-mer by extending bases one by one include an (N-1)-mer which is shorter by one base and an (N-2)-mer which is shorter by two bases, generated in coupling steps. Such (N-1)-mer and (N-2)-mer are very similar in structure and physical properties to the target N-mer. As a result, in the stage of purifying the N-mer using chromatography or the like, the difference in mobility between the target N-mer and the by-products such as (N-1)-mer and (N-2)-mer is small. For this reason, there exists a problem of a heavy burden imposed by purification for precisely separating the N-mer and others.

In addition, in general-purpose oligonucleotide synthesis, a solid-phase synthesis method including extending chain in the 5'-direction of a nucleoside with a 3'-terminal fixed to a solid-support is employed. In the method, a commercially available monomer amidite for use in solid-phase synthesis is required to be purchased or a monomer amidite is required to be self-prepared by an experimenter. In general, commercially available monomer amidites are expensive, obstructing a large amount of target oligonucleotides to be synthesized. Also, in the case of self-preparation by an experimenter, a target monomer amidite at high purity is required to be prepared at high yield. The reason is that use of a not high-purity monomer nucleotide has a negative effect on the coupling reaction in oligonucleotide synthesis with high probability.

In view of such circumstances, it is an object of the present invention to provide a segment for use in synthesis of a large amount of oligonucleotide which can be more conveniently purified, a method for producing the same, and a method for synthesizing an oligonucleotide using the same.

Solution to Problem

In order to solve the problems, the segment for use in synthesis of an oligonucleotide, a method for producing the same, and a method for synthesizing an oligonucleotide using the same according to the present invention employ the following means.

A first aspect of the present invention relates to a segment for use in synthesis of an oligonucleotide, represented by the following formula (I).

[Chemical Formula 1]

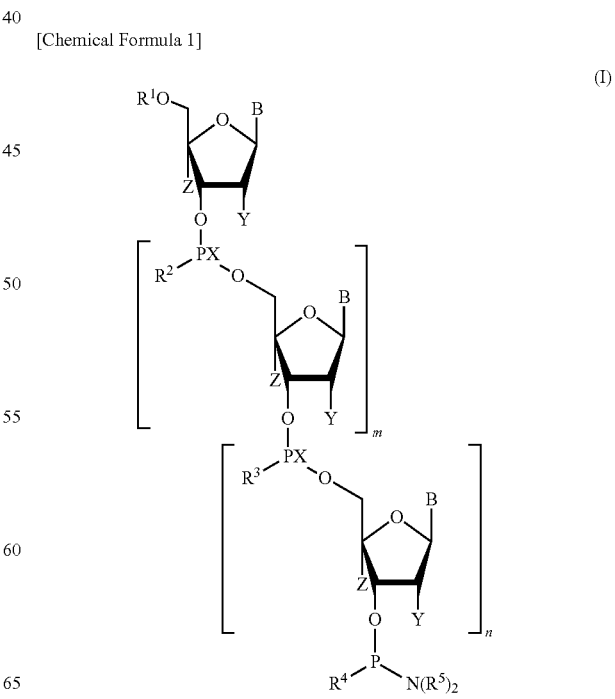

(I)

In formula (I), B is independently a protected or unprotected nucleoside base; $R^1$ is a protecting group; $R^2$, $R^3$ and $R^4$ are independently $OCH_2CH_2CN$, $SCH_2CH_2CN$, $OCH_2CH=CH_2$, or $OCH_3$; $R^5$ is a substituted or unsubstituted aliphatic group, or a substituted or unsubstituted aromatic group; X is independently a lone pair, =O or =S; Y is independently H, $NHR^6$, a halogen, CN, $CF_3$ or a hydroxyl group protected with an acyl protecting group, an ether protecting group or a silyl protecting group; $R^6$ is H, an aliphatic group or an aromatic group; Z is independently H, an alkyl, an O-alkyl, an N-alkyl or a halogen, or forms a Z-Y bond with Y; and (m+n) is an integer of 2 or more and 23 or less.

In the first aspect described above, in the case where B in formula (I) is a nucleoside base protected with a protecting group, the protecting group may be an acyl protecting group.

In the first aspect, in formula (I), $R^1$ may be a protecting group removable under acidic conditions or a trialkylsilyl group; Y may be preferably H or a hydroxyl group protected with a t-butyldimethylsilyl group; Z may be preferably H; and $R^5$ may be an isopropyl group.

A second aspect of the present invention relates to a method for producing a segment for use in synthesis of an oligonucleotide, represented by the following formula (I).

[Chemical Formula 2]

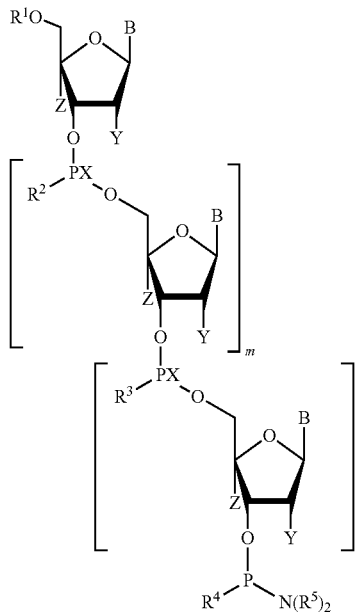

(I)

In formula (I), B is independently a protected or unprotected nucleoside base; $R^1$ is a protecting group; $R^2$, $R^3$ and $R^4$ are independently $OCH_2CH_2CN$, $SCH_2CH_2CN$, $OCH_2CH=CH_2$, or $OCH_3$; $R^5$ is a substituted or unsubstituted aliphatic group, or a substituted or unsubstituted aromatic group; X is independently a lone pair, =O or =S; Y is independently H, $NHR^6$, a halogen, CN, $CF_3$ or a hydroxyl group protected with an acyl protecting group, an ether protecting group or a silyl protecting group; $R^6$ is H, an aliphatic group or an aromatic group; Z is independently H, an alkyl, an O-alkyl, an N-alkyl or a halogen, or forms a Z-Y bond with Y; and (m+n) is an integer of 2 or more and 23 or less.

The production method comprises:

(a) a step of reacting a nucleoside represented by the following formula (II):

[Chemical Formula 3]

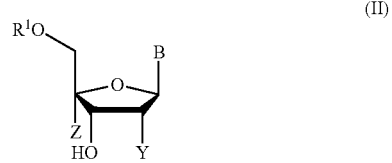

(II)

with a phosphitylating compound having a structure of $R^2P\{N(R^1)_2\}_2$ and a nucleoside having a structure of the following formula (III):

[Chemical Formula 4]

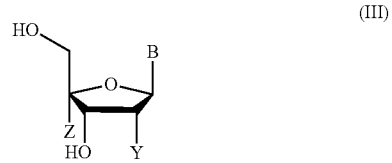

(III)

to prepare a compound having a structure of the following formula (IV):

[Chemical Formula 5]

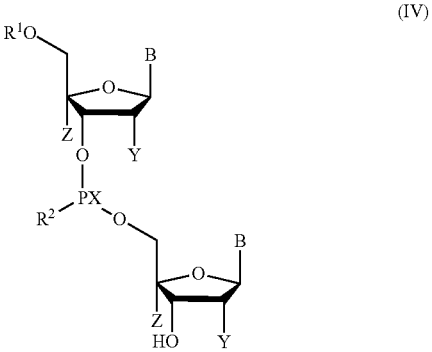

(IV)

(b) a step of reacting the compound having a structure of formula (IV) with a phosphitylating compound having a structure of $R^3P\{N(R^5)_2\}_2$ and a nucleoside having a structure of formula (III) or a compound having a structure of the following formula (V):

[Chemical Formula 6]

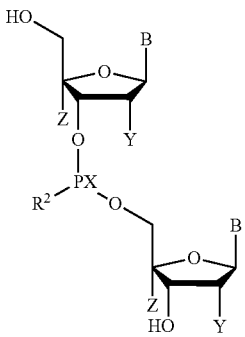

(V)

or a compound having a structure of the following formula (VI):

[Chemical Formula 7]

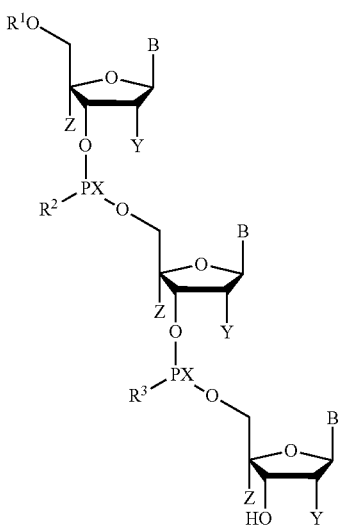

(VI)

to prepare a compound having a structure of the following formula (VII):

[Chemical Formula 8]

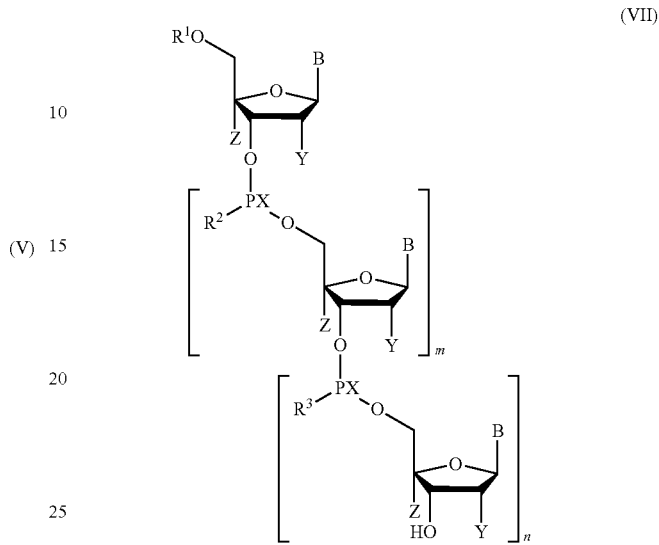

(VII)

(c) a step of repeating the step (b) at least one time on an as needed basis; and (d) a step of reacting the resulting intermediate with a phosphitylating compound having a structure of $R^4P\{N(R^5)_2\}_2$ to prepare a segment having a structure of formula (I).

In the second aspect, in the case where B in formula (I) is a nucleoside protected with a protecting group, the protecting group may be an acyl protecting group.

In the second aspect, in formula (I), $R^1$ may be a protecting group removable under acidic conditions or a trialkylsilyl group; Y may be preferably H or a hydroxyl group protected with a t-butyldimethylsilyl group; Z may be preferably H, and $R^5$ may be an isopropyl group.

In the second aspect, a step of reacting the compound represented by formula (IV) obtained in the step (a) or the compound represented by formula (VII) obtained in the step (b) with an oxidizing agent or sulfurizing agent may be included on an as needed basis.

A third aspect of the present invention relates to a method for synthesizing an oligonucleotide using a segment for use in synthesis of an oligonucleotide, represented by formula (I).

The synthesis method includes (a) a condensation step of condensing an amidite moiety of the segment for use in synthesis of an oligonucleotide represented by formula (I) with a hydroxyl group of a nucleoside or nucleotide, (b) an oxidation step of oxidizing a phosphite-linkage position obtained in the condensation step, and (c) a deprotection step of deprotecting the terminal protecting group of the segment for use in synthesis of an oligonucleotide condensed with a nucleoside or nucleotide in the condensation step.

In the third aspect, each of the steps may be performed in a solution.

In the third aspect, each of the steps may be performed on a solid-support.

Advantageous Effects of Invention

According to the segment for use in synthesis of an oligonucleotide of the present invention, compared with the case in which an oligonucleotide is synthesized using a general-purpose monomer amidite step by step, the number of steps can be reduced. The yield of the oligonucleotide having a target length can be therefore improved than that of a conventional method.

Further, in the case where an N-mer oligonucleotide is synthesized using the segment for use in synthesis of an oligonucleotide of the present invention, no by-product having a length of N-1 to N-3 is produced. For this reason, it is possible to reduce the purification burden of a target N-mer oligonucleotide, so that the purification can be performed more conveniently, and a larger amount of the target product can be supplied.

DESCRIPTION OF EMBODIMENTS

Figure 1:
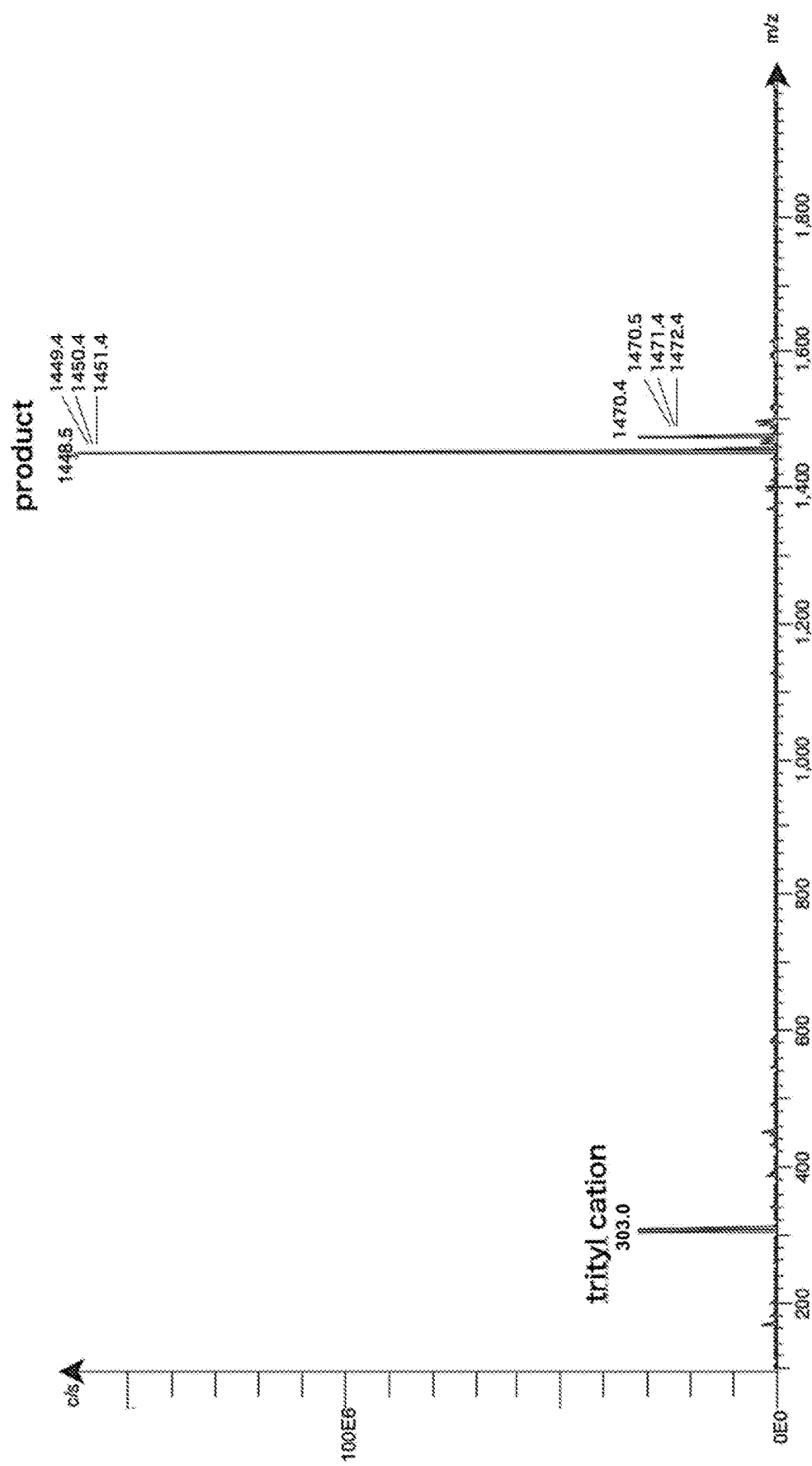
FIG. 1 is a chart showing an ESI-MS spectrum of a dT trimer amidite, which is the segment for use in synthesis of an oligonucleotide obtained in Example 1.

Hereinafter, an embodiment for obtaining the segment for use in synthesis of an oligonucleotide of the present invention is described.

The segment for use in synthesis of an oligonucleotide in the present embodiment has a structure represented by the following formula (I):

[Chemical Formula 9]

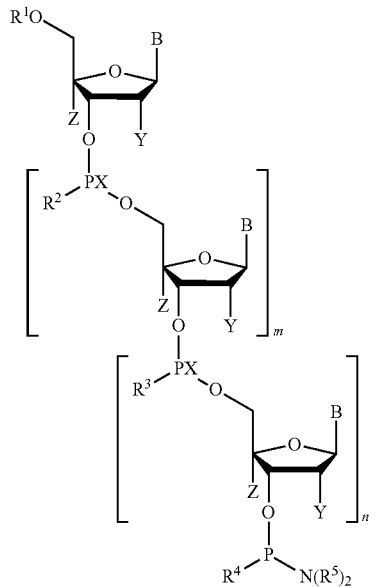

(I)

In formula (I), B is independently a protected or unprotected nucleoside base; $R^1$ is a protecting group; $R^2$, $R^3$ and $R^4$ are independently $OCH_2CH_2CN$, $SCH_2CH_2CN$, $OCH_2CH=CH_2$, or $OCH_3$; $R^5$ is a substituted or unsubstituted aliphatic group, or a substituted or unsubstituted aromatic group; X is independently a lone pair, =O or =S; Y is independently H, $NHR^6$, a halogen, CN, $CF_3$ or a hydroxyl group protected with an acyl protecting group, an ether protecting group or a silyl protecting group; $R^6$ is H, an aliphatic group or an aromatic group; Z is independently H, an alkyl, an O-alkyl, an N-alkyl or a halogen, or forms a Z-Y bond with Y; and (m+n) is an integer of 2 or more and 23 or less.

The segment for use in synthesis of an oligonucleotide in the present embodiment is obtained by the following successive steps (1) and (2).

(1) Using a nucleoside having a 5'-hydroxyl group and, on as needed basis, a nucleoside base moiety, protected with a protecting group, and an unprotected 3'-hydroxyl group (hereinafter referred to as "5'-protected/3'-unprotected nucleoside") as a starting material, the 3'-hydroxyl group is phosphitylated to obtain 3'-phosphoramidite as an intermediate in situ.

(2) The resulting intermediate is reacted with the 5'-hydroxyl group of a nucleoside having a nucleoside base moiety protected with a protecting group on an as needed basis, and, on the other hand, both of the 3'-hydroxyl group and the 5'-hydroxyl group unprotected (hereinafter referred to as "3'-, 5'-unprotected nucleoside"). The unprotected 3'-hydroxyl group remaining on a 3'-terminal is reacted with a phosphitylating agent to produce a phosphoramidite.

An (n+1)mer nucleotide phosphoramidite is synthesized by repeating the step (2) as many times as required (n times).

In contrast, in the case where a nucleotide dimer or trimer is synthesized by a conventional method, it is necessary to perform a reaction for protecting the 3'-hydroxyl group of a 5'-protected/3'-unprotected nucleoside, and then perform a reaction for removing the protecting group for 5'-hydroxyl group only, so that a nucleoside having the 3'-hydroxyl group and, on an as needed basis, a nucleoside base moiety, protected with a protecting group and the 5'-hydroxyl group unprotected (hereinafter referred to as "5'-unprotected/3'-protected nucleoside") is prepared in advance. In contrast, in the present embodiment, a nucleoside having both of the 5'-hydroxyl group and the 3'-hydroxyl group unprotected, with one protecting group less than those of a conventional method, can be used for synthesis of the segment. The 3', 5'-unprotected nucleoside as one of the main raw materials in synthesis of the segment can be therefore prepared in a smaller number of steps compared with a conventional method, so that a larger amount can be synthesized at low cost in a short time.

The nucleoside base in the present embodiment includes a natural base such as an adenyl group, a guanyl group, a cytosinyl group, a thyminyl group and an uracil group, and a modified base such as a 5-methylcytosinyl group, a 5-fluorouracil group, a 7-methylguanyl group and a 7-deazaadenyl group. The amino group in these nucleoside bases includes a benzyl protecting group, an allyl protecting group, a carbamate protecting group and an acyl protecting group. Preferably, an acyl protecting group such as an acetyl group, a benzoyl group, a phenoxyacetyl group, and an isopropylcarbonyl group is used.

The aliphatic group in the present embodiment includes a saturated or unsaturated, linear or branched $C_1$-$C_{18}$ hydrocarbon, and a saturated or unsaturated cyclic $C_3$-$C_{18}$ hydrocarbon. A saturated or unsaturated $C_1$-$C_8$ hydrocarbon or a cyclic $C_3$-$C_8$ hydrocarbon is preferred. The aromatic group in the present embodiment includes a carbocyclic aromatic ring such as a phenyl group, and a carbocyclic aromatic ring condensed with a carbocyclic aromatic ring or a non-carbocyclic aromatic ring such as a naphthyl group. The aliphatic group and the aromatic group in the present embodiment may be substituted with a substituent such as a saturated or unsaturated $C_1$-$C_8$ hydrocarbon or $C_3$-$C_8$ cyclic hydrocarbon, a halogen, a cyano group, a nitro group, and an aromatic ring.

The protecting groups for 5'-, 3'- or 2'-hydroxyl group in the present embodiment include a protecting group removable under acidic conditions, an acyl protecting group, and a silyl protecting group. The protecting groups removable under acidic conditions include an ether protecting group including a substituted or unsubstituted trityl group, a pixyl group, and a substituted or unsubstituted tetrahydropyranyl (THP) group, and 4,4'-dimethoxytrityl group is a typical protecting group. The silyl protecting groups include a trimethylsilyl group, a triethylsilyl group, a t-butyldimethylsilyl group, a t-butyldiphenylsilyl group, and a triphenylsilyl group. The acyl protecting groups include an acetyl group and a benzoyl group. Alternatively, a nucleoside with a crosslink bond between the 5'-position and the 2'-position may be used as a raw material. In this case, between the 5'-position and the 2'-position, a bond of (5'-position)-L-O-(2'-position) can be formed, and examples of L include a $C_1$-$C_6$ alkylene group, wherein the intermediate carbon atom may be substituted with an oxygen atom or a nitrogen atom to which an alkyl group is bonded.

In the step (1), after reacting the 3'-hydroxyl group of the 5'-protected/3'-unprotected nucleoside with a phosphitylating agent to produce 3'-phosphoramidite in situ, an activator that activates the amidite moiety is added to the resulting 3'-phosphoramidite without isolation and purification to cause a reaction with 3', 5'-unprotected nucleoside, so that an extension by one base unit is achieved. Further, through a reaction with a phosphitylating agent, 3'-phosphoramidite is produced. Typical examples of the phosphitylating agent include $NCCH_2CH_2OP[N(i-C_3H_7)_2]_2$ and $CH_2=CHCH_2OP[N(i-C_3H_7)_2]_2$, though not limited thereto. Typical examples of the activator include 1H-tetrazole, S-ethylthio-1H-tetrazole, dicyanoimidazole, and a salt of sulfonic acid and azole or tertiary amine, though not limited thereto. The reaction is performed in a dried solvent such as dichloromethane, acetonitrile, tetrahydrofuran, DMF and toluene.

In the step (1), to a solution of 5'-protected/3'-unprotected nucleoside (0.2 to 0.4 M), a phosphitylating agent (1.05 to 1.2 equivalents of 5'-protected/3'-unprotected nucleoside) and an activator (0.4 to 0.7 equivalents of 5'-protected/3'-unprotected nucleoside) are added and stirred at room temperature for 2 to 5 hours. The resulting 3'-phosphoramidite is purified on silica gel, and then a subsequent step (2) is performed.

In the step (2), to the 3'-phosphoramidite obtained in the step (1), 3', 5'-unprotected nucleoside (1.3 to 2.0 equivalents of 5'-protected/3'-unprotected nucleoside) and an activator (2 to 3 equivalents of 5'-protected/3'-unprotected nucleoside) are added to cause a reaction at room temperature for 0.5 to 1.5 hours, and through silica gel filtration and concentration of the filtrate, a nucleotide intermediate having an unprotected hydroxyl group at a 3'-terminal, with extension by one base unit, is obtained. The yield is about 60 to 95%. The solution of the nucleotide intermediate (0.05 to 0.4 M) is reacted with a phosphitylating agent (1.2 to 2.0 equivalents of 5'-protected/3'-unprotected nucleoside) and an activator (0.5 to 1.0 equivalent of 5'-protected/3'-unprotected nucleotide) to obtain 3'-phophoroamidite of a trimer nucleotide. On an as needed basis, the step (2) is further performed to obtain a tetramer or more nucleotide. In the case where a tetramer or more segment is synthesized, as an alternative for the method of extending one base each at a time, segments already being a dimer or more may be condensed to each other to achieve extension by two or more base units at a time.

Synthesis of an oligonucleotide using the segment for use in synthesis of oligonucleotide represented by formula (I) may be performed in a solution (hereinafter referred to as "liquid-phase synthesis method"), or may be performed on a solid-support (hereinafter referred to as "solid-phase synthesis method"). In the case where the synthesis is performed by the liquid-phase synthesis method, the nucleoside at the 3' end of the nucleoside or nucleotide having a 3'-hydroxyl group to which a silyl protecting group or an aliphatic-containing protecting group introduced to increase the solubility in the reaction solvent is used to be subjected to repetition of a condensation step (a) of condensation with a segment for use in synthesis of an oligonucleotide represented by formula (I), an oxidation or sulfurization step (b) of oxidizing or sulfurizing the phosphite-linkage position, and a deprotection step (c) of deprotecting the terminal protecting group of the segment for synthesis of an oligonucleotide condensed with nucleoside or nucleotide in the condensation step. In the case where the synthesis is performed by the solid-phase synthesis method, a condensation step (a) of condensation with a segment for use in synthesis of an oligonucleotide represented by formula (I), a capping step (b) of capping the unreacted 5'-hydroxyl group of nucleoside or nucleotide on a solid-support, an oxidation step (c) of oxidizing the phosphite-linkage position, and a deprotection step (d) of deprotecting the terminal protecting group of the segment for synthesis of an oligonucleotide condensed with nucleoside or nucleotide in the condensation step are repeated. In both of the methods, a target oligonucleotide can be obtained through a subsequent treatment under basic conditions.

Specifically, in either case of using the liquid-phase synthesis method and the solid-phase synthesis method, as the first step of oligonucleotide synthesis, a reaction for activating the 3'-terminal amidite of the segment for use in synthesis of an oligonucleotide represented by formula (I) with an activator so as to be condensed with a nucleoside or nucleotide having 5'-unprotected hydroxyl group is performed. As the activator, a commonly used phosphite activator may be used, and examples thereof include 1H-tetrazole, S-ethylthio-1H-tetrazole, dicyanoimidazole, and a salt of sulfonic acid and azole or a tertiary amine, though not limited thereto. The time required for the condensation reaction is generally about 1 minute to 30 minutes, depending on the scale of the reaction.

Next, as a second step in synthesis of an oligonucleotide, the intermediate obtained in the condensation step is reacted with an oxidizing agent or a sulfurizing agent to obtain a pentavalent phosphate or a thiophosphate nucleotide.

Subsequently, as a third step in the oligonucleotide synthesis, the intermediate obtained in the oxidation or sulfurization reaction is reacted with an anhydrous acidic solution to obtain a nucleotide with 5'-hydroxyl group unprotected.

In the oligonucleotide synthesized by using the segment for use in synthesis of an oligonucleotide in the present embodiment, a protecting group for the nucleoside base, a protecting group for the 5'-, 3'- or 2'-hydroxyl group, and a protecting group for phosphoric acid in the phosphate bond are deprotected under deprotection conditions corresponding to the protecting group used.

The following Examples illustrate an embodiment of the present invention. According to the procedure shown in Example 1 and Examples 2, a tetramer phosphoramidite which is one of the segments for use in synthesis of an oligonucleotide represented by formula (I) was synthesized. Also, according to the procedure shown in Example 3, a pentamer phosphoramidite which is one of the segments for use in synthesis of an oligonucleotide represented by formula (I) was synthesized. Further, according to the procedure shown in Example 4, an oligonucleotide 18-mer was synthesized using a trimer phosphoramidite which is one example of the compounds represented by formula (I).

[Example 1] Synthesis of Tetramer Phosphoramidite (3)

Step 1: Synthesis of DMTr-T$_{p(OCH2CH2CN)}$T$_{(OCH2CH2CN)(N(i-C3H7)2)}$(1)

[Chemical Formula 10]

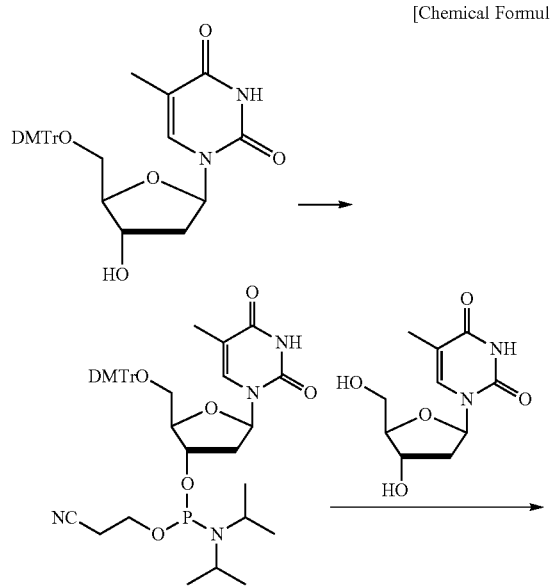

To a dichloromethane solution (90 mL) of 5'-O-DMTr thymidine (16.3 g, 30.0 mmol), a phosphitylating agent NCCH$_2$CH$_2$OP[N(i-C$_3$H$_7$)$_2$]$_2$ (10.5 mL, 33.0 mmol), diisopropylamine (2.12 mL, 15.0 mmol), and 1H-tetrazole (1.05 g, 15.0 mmol) were added in this order at room temperature. After stirring at room temperature for 3 hours, the reaction solution was added to a dimethylformamide (DMF) solution (90 mL) of thymidine (10.9 g, 45.0 mmol) and 1H-tetrazole (5.25 g, 75.0 mmol), and stirred for 1 hour at room temperature. After adding 180 mL of dichloromethane to the reaction solution, the mixture was applied to 340 g of silica gel for washing with dichloromethane. The resulting filtrate was concentrated under reduced pressure to obtain an intermediate. After the intermediate was dissolved in dichloromethane (180 mL), a phosphitylating agent NCCH$_2$CH$_2$OP[N(i-C$_3$H$_7$)$_2$]$_2$ (12.4 mL, 39.0 mmol) and 1H-tetrazole (1.05 g, 15.0 mmol) were added in this order at room temperature. After stirring at room temperature for 3 hours, purification was performed by silica gel column chromatography using dichloromethane-IPA as an elution solvent to obtain a target phosphoramidite 1 (24.2 g, yield: 74.4%).

MS: 1108.4 (MNa$^+$)

Step 2: Synthesis of DMTr-T$_{p(OCH2CH2CN)}$T$_{p(OCH2CH2CN)}$T$_{(OCH2CH2CN)(N(i-C3H7)2)}$ (2)

[Chemical Formula 11]

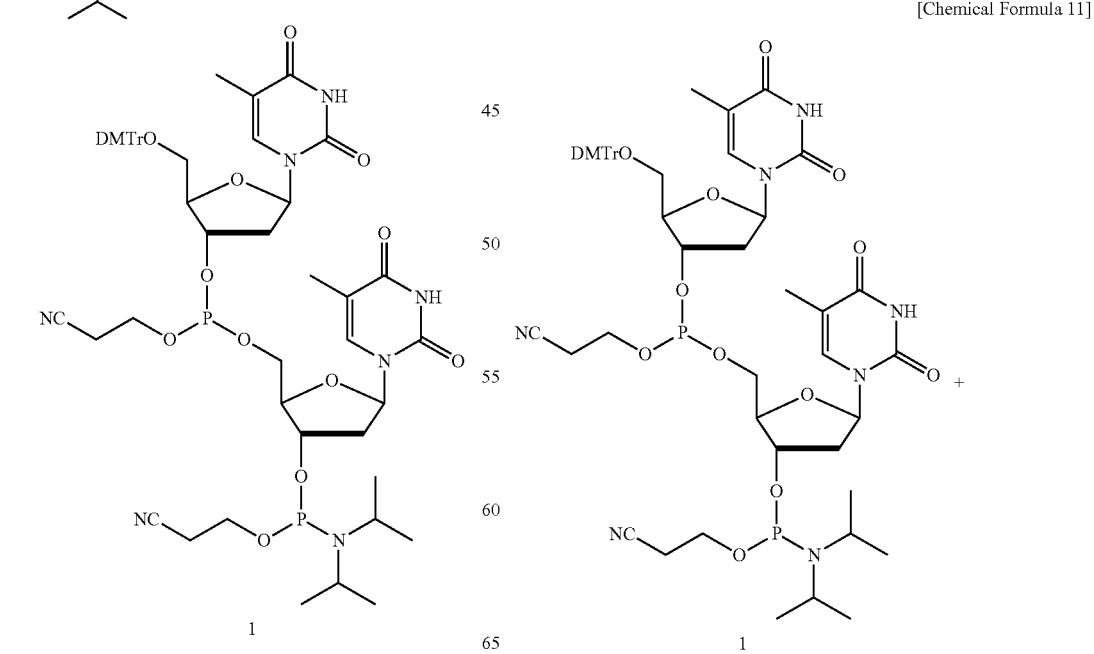

-continued

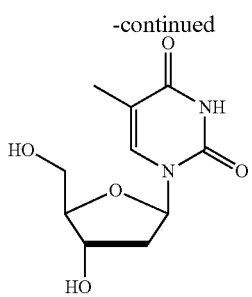

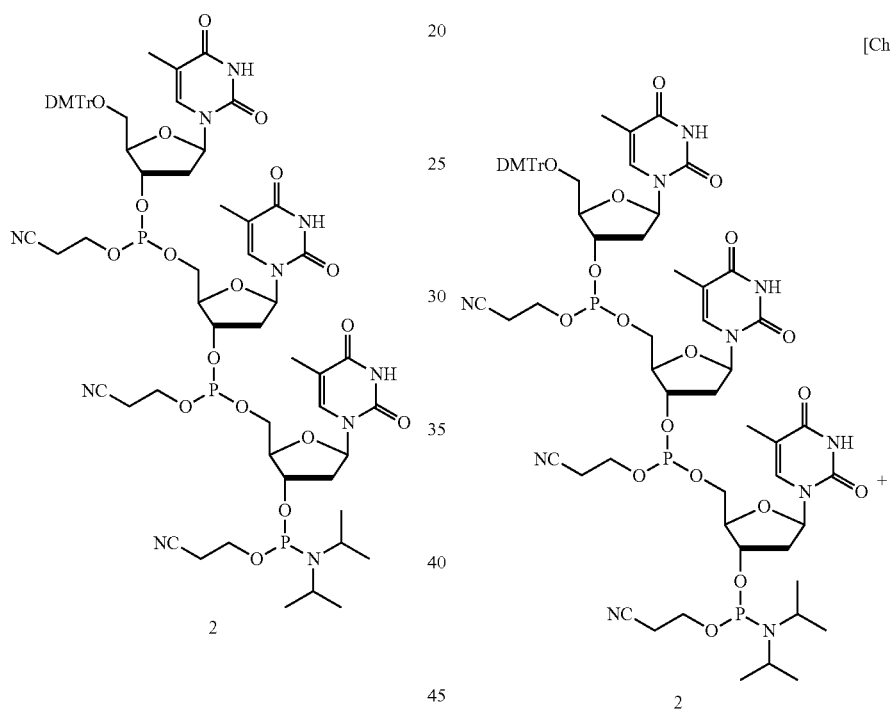

Figure 2:
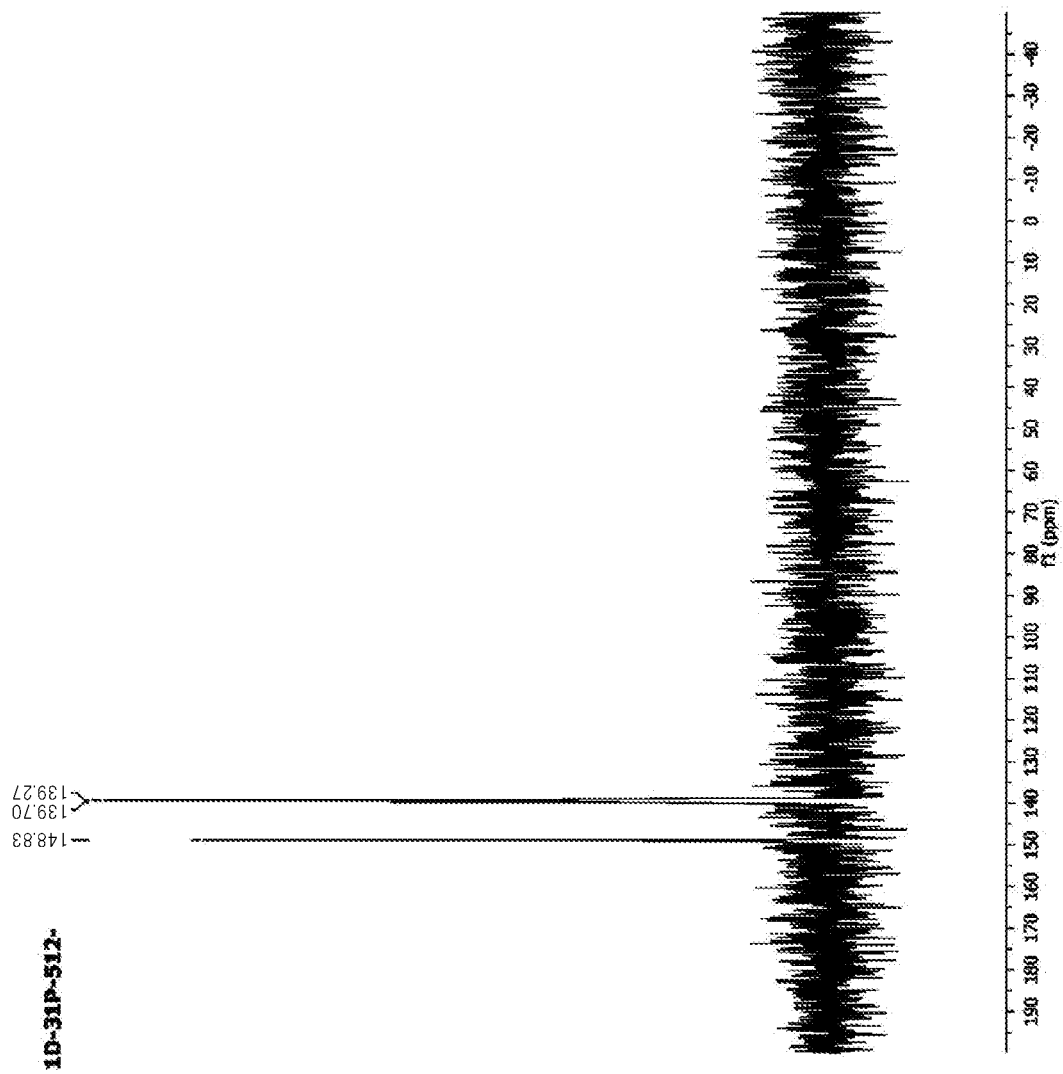
FIG. 2 is a chart showing $^{31}$P NMR spectrum of a dT trimer amidite, which is the segment for use in synthesis of an oligonucleotide obtained in Example 1.

ESI-MS spectrum of the resulting phosphoramidite 2 is shown in FIG. 1, and a $^{31}$P NMR spectrum thereof is shown in FIG. 2, respectively.

MS: 1448.5 (MNa$^+$)

Step 3: Synthesis of DMTr-T$_{p\ (OCH2CH2CN)}$ T$_{p(OCH2CH2CN)}$T$_{p(OCH2CH2CN)}$ T$_{p(OCH2CH2CN)\ (N\ (i\text{-}C3H7)2)}$ (3)

[Chemical Formula 12]

A dichloromethane solution (23 mL) of the phosphoramidite 1 (10.0 g, 9.21 mmol) was added dropwise to a DMF solution (30 mL) of thymidine (2.90 g, 12.0 mmol) and 1H-tetrazole (1.94 g, 27.6 mmol) and stirred at room temperature for 1 hour. Dichloromethane (46 mL) was added to the reaction solution, and the mixture was then applied to 340 g of silica gel for washing with dichloromethane. The filtrate was concentrated and then dissolved in a dichloromethane solution (81 mL), and a phosphitylating agent NCCH$_2$CH$_2$OP[N(i-C$_3$H$_7$)$_2$]$_2$ (3.19 mL, 10.6 mmol) and 1H-tetrazole (0.4 g, 5.70 mmol) were added thereto in this order at room temperature. After stirring at room temperature for 3 hours, the product was dissolved in dichloromethane (163 mL) and purified by silica gel column chromatography using dichloromethane-IPA as an elution solvent to obtain a target phosphoramidite 2 (9.65 g, yield: 73.4%). An

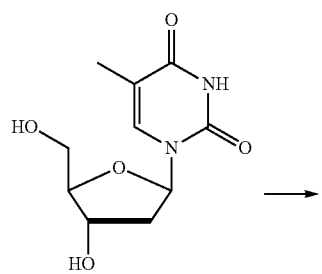

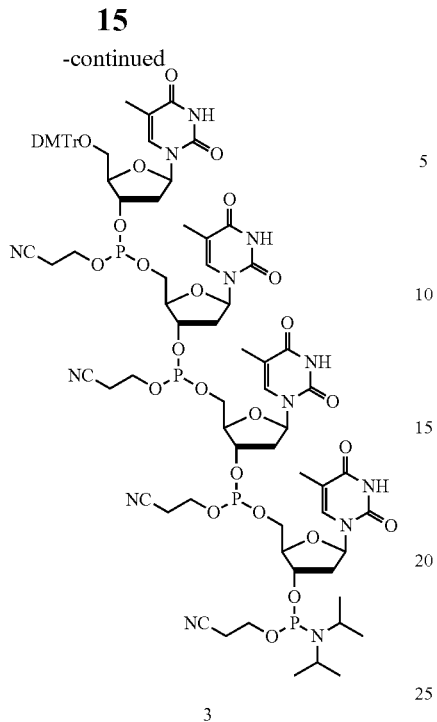

3

A dichloromethane solution (70 mL) of the phosphoramidite 2 (10.0 g, 7.01 mmol) was added to a DMF solution (90 mL) of thymidine (2.21 g, 9.11 mmol) and 1H-tetrazole (1.47 g, 21.2 mmol) and stirred at room temperature for 1 hour. After adding dichloromethane (140 mL) to the reaction solution, the mixture was applied to 340 g of silica gel for washing with dichloromethane. The filtrate was concentrated and then dissolved in a dichloromethane solution (70 mL), and a phosphitylating agent $NCCH_2CH_2OP[N(i-C_3H_7)_2]_2$ (2.89 mL, 9.11 mmol) and 1H-tetrazole (0.340 g, 4.90 mmol) were added thereto in this order at room temperature. After stirring at room temperature for 3 hours, the product was dissolved in dichloromethane (140 mL) and purified by silica gel column chromatography using dichloromethane-IPA as an elution solvent to obtain a target tetramer phosphoramidite 3 (9.40 g, Yield: 75.9%).

MS: 1791.6 ($MNa^+$)

[Example 2] Synthesis of Tetrameric Phosphoramidite (6)

Step 4: Synthesis of DMTr-$T_{p(OCH2CH2CN)}C_{(OCH2CH2CN) (N(i-C3H7)2)}$ (4)

[Chemical Formula 13]

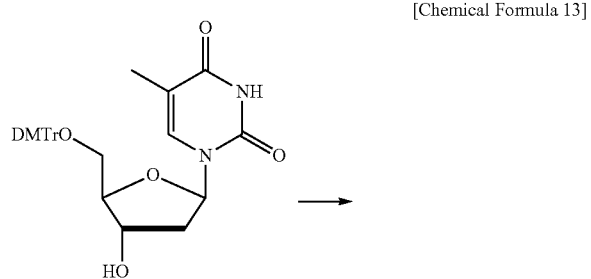

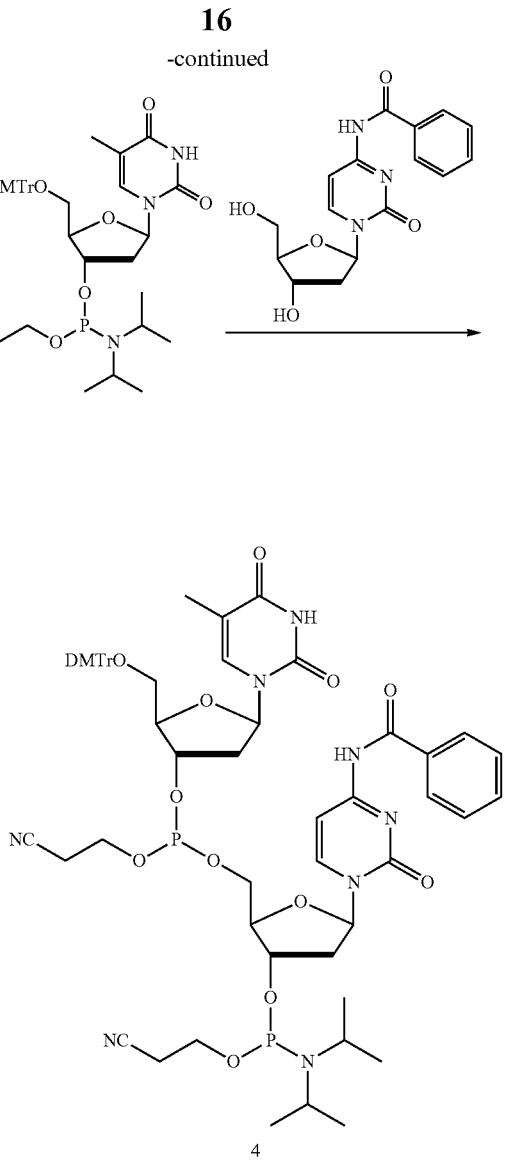

4

To a dichloromethane solution (90 mL) of 5'-O-DMTr thymidine (16.3 g, 30.0 mmol), a phosphitylating agent $NCCH_2CH_2OP[N(i-C_3H_7)_2]_2$ (10.5 mL, 33.0 mmol), diisopropylamine (2.12 mL, 15.0 mmol), and 1H-tetrazole (1.05 g, 15.0 mmol) were added in this order at room temperature. After stirring at room temperature for 3 hours, the reaction solution was added to a DMF solution (90 mL) of $N^4$-benzoylcytidine (12.9 g, 39.0 mmol) and 1H-tetrazole (6.31 g, 90.0 mmol), and stirred at room temperature for 1 hour. After adding 180 mL of dichloromethane to the reaction solution, a phosphitylating agent $NCCH_2CH_2OP[N(i-C_3H_7)_2]_2$ (12.4 mL, 39.0 mmol) and 1H-tetrazole (1.05 g, 15.0 mmol) were added in this order at room temperature. After stirring at room temperature for 3 hours, the mixture was applied to 340 g of silica gel for washing with dichloromethane. The resulting filtrate was concentrated under reduced pressure to obtain an intermediate (yield: 70 to 90%). The intermediate was dissolved in dichloromethane (180 mL) and purified by silica gel column chromatography using dichloromethane-IPA as an elution solvent to obtain a target phosphoramidite 4 (27.1 g, yield: 77.0%).

MS: 1197.4 ($MNa^+$)

Step 5: Synthesis of dG$_{p(OCH2CH2CN)}$T (5)

[Chemical Formula 14]

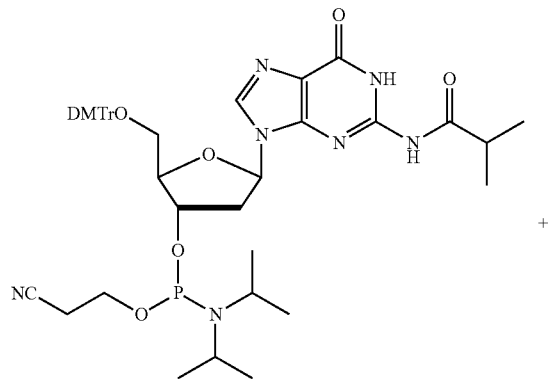

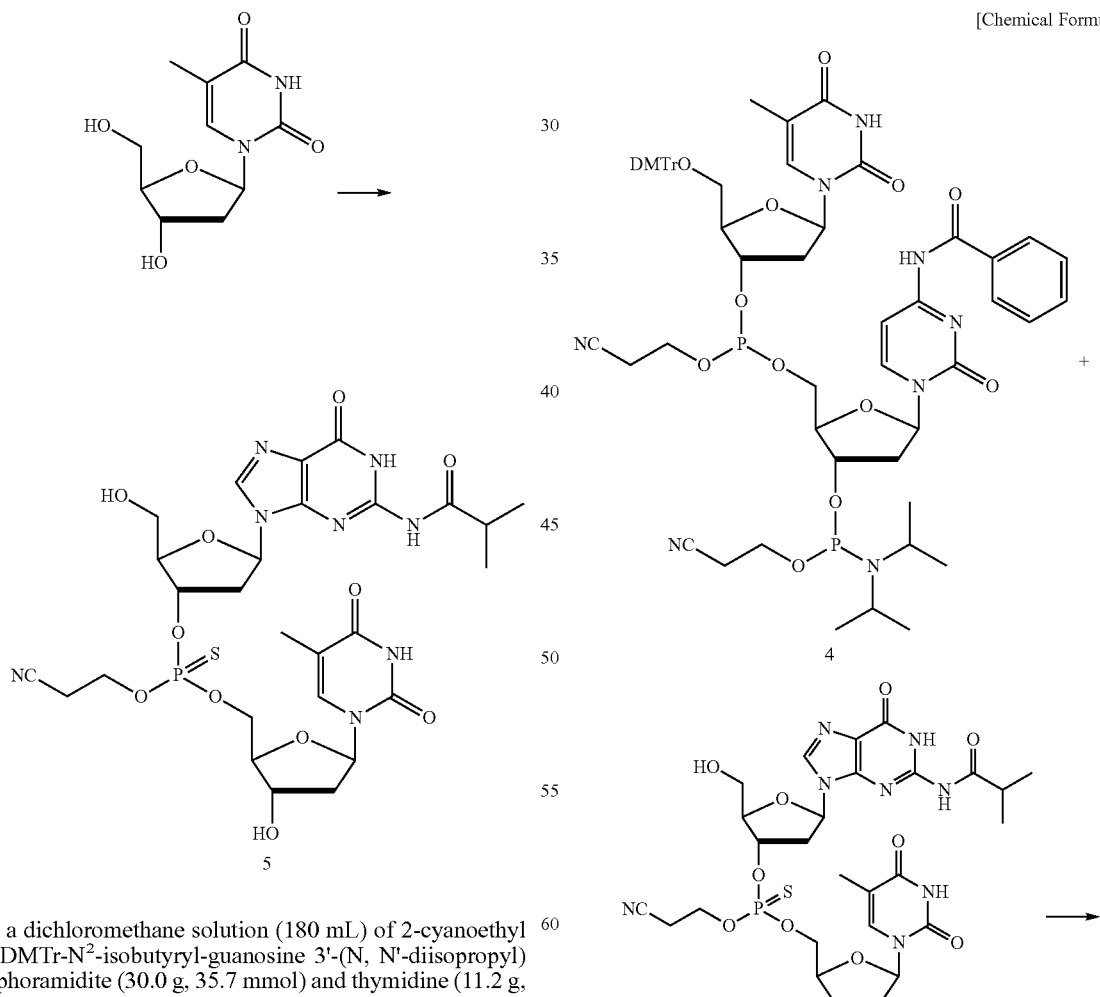

To a dichloromethane solution (180 mL) of 2-cyanoethyl 5'-O-DMTr-N$^2$-isobutyryl-guanosine 3'-(N, N'-diisopropyl) phosphoramidite (30.0 g, 35.7 mmol) and thymidine (11.2 g, 46.4 mmol), 1H-tetrazole (7.50 g, 107 mmol) was added, and the mixture was stirred at room temperature for 1 hour. To the reaction solution, phenylacetyl disulfide (32.4 g, 107 mmol) was added, and the mixture was further stirred for 1 hour. After adding 180 mL of dichloromethane, the mixture was applied to 340 g of silica gel for washing with dichloromethane. The resulting filtrate was concentrated under reduced pressure to obtain a product (yield: 70 to 90%). After dissolving in dichloromethane (180 mL), the solution was purified by silica gel column chromatography using dichloromethane-IPA as an elution solvent to obtain an intermediate (yield: 70 to 90%). To the intermediate (15 g, 15.3 mmol), 1000 mL of a dichloromethane solution of 3% dichloroacetic acid was added at 0° C., and the mixture was stirred at room temperature for 30 minutes. The reaction solution was applied to 1500 g of silica gel for washing with ethyl acetate. Further, purification by silica gel column chromatography using dichloromethane-IPA as an elution solvent was performed to obtain a target dimer 5 (22.1 g, yield: 87.3%).

MS: 723.2 (MNa$^+$)

(Step 6: Synthesis of DMTr-T$_{p(OCH2CH2CN)}$ C$_{(OCH2CH2CN)}$G$_{p(OCH2CH2CN)}$ T$_{(OCH2CH2CN)}$ $_{(N(i-C3H7)2)}$ (6)

[Chemical Formula 15]

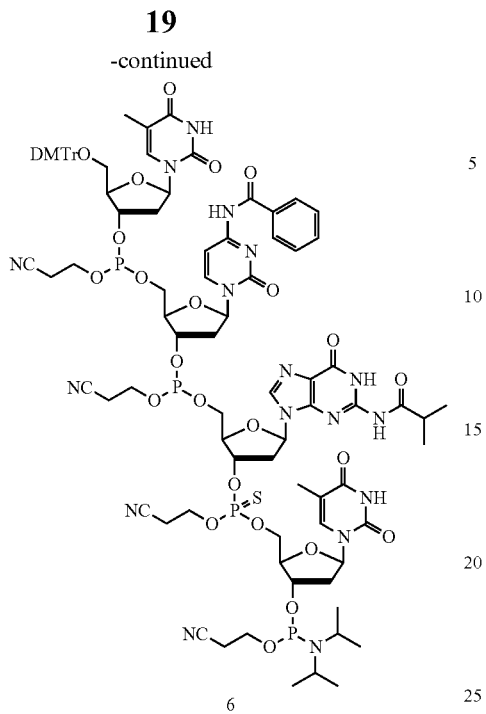

A dichloromethane solution (50 mL) of the compound 4 (10.0 g, 8.51 mmol) was added dropwise to a DMF solution (45 mL) of the compound 5 (7.26 g, 10.2 mmol) and 1H-tetrazole (1.79 g, 25.5 mmol), and stirred at room temperature for 1 hour. After adding dichloromethane (90 mL) to the reaction solution, the mixture was applied to 340 g of silica gel for washing with dichloromethane. The filtrate was concentrated and then dissolved in a dichloromethane solution (85 mL), and a phosphitylating agent $NCCH_2CH_2OP[N(i-C_3H_7)_2]_2$ (3.19 mL, 10.6 mmol) and 1H-tetrazole (0.420 g, 5.96 mmol) were added in this order at room temperature. After stirring at room temperature for 3 hours, the mixture was dissolved in dichloromethane (170 mL) and purified by silica gel column chromatography using dichloromethane-IPA as an elution solvent to obtain a target phosphoramidite 6 (9.42 g, yield: 63.1%).

MS: 1974.6 (MNa$^+$)

[Example 3] Synthesis of Pentamer Amidite (15)

Step 7: Synthesis of DMTr-A$^{Bz}_{p(OCH2CH=CH2)}$ (8)

[Chemical Formula 16]

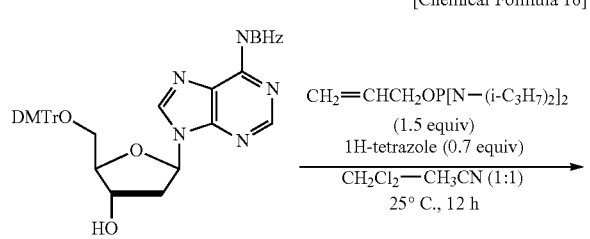

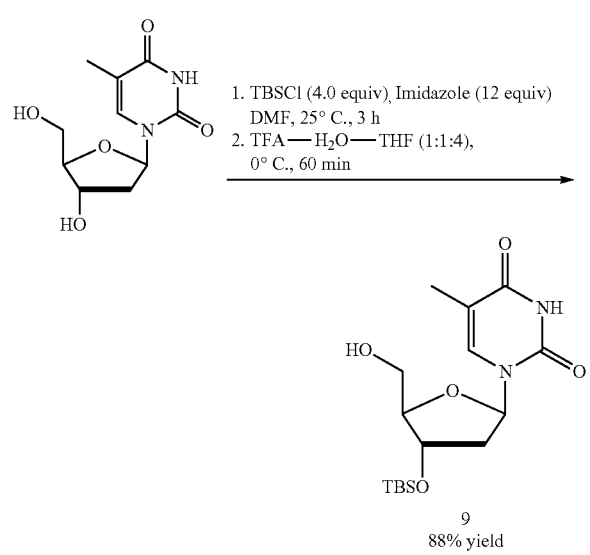

To a dichloromethane-acetonitrile (1:1) solution (20 mL) of 5'-O-DMTr-N$^5$-benzoyl 2'-deoxyadenosine (7) (3.3 g, 5.0 mmol), a phosphitylating agent $CH_2=CHCH_2OP[N(i-C_3H_7)_2]_2$ (2.3 mL, 7.5 mmol) and 1H-tetrazole (0.25 g, 3.5 mmol) were added in two parts at 0° C. After stirring at room temperature for 12 hours, dichloromethane (60 mL) was added, and purification was performed by silica gel column chromatography using hexane-ethyl acetate as an elution solvent to obtain a target phosphoramidite 8 (4.0 g, yield: 94%).

Step 8: Synthesis of 3'-TBS-T (9)

[Chemical Formula 17]

To a DMF solution (200 mL) of thymidine (10 g, 41 mmol), imidazole (33 g, 500 mmol) and tert-butyldimethylsilyl chloride (25 g, 170 mmol) were added in two parts. After stirring at room temperature for 3 hours, 5 mL of methanol was added to the reaction solution and the mixture was added dropwise to distilled water (1000 mL). The residue was filtered off and dissolved in THF. Trifluoroacetic acid (40 mL) and distilled water (40 mL) were added thereto at 0° C. and stirred for 1 hour. The reaction solution was added dropwise to distilled water (500 mL) and extracted with dichloromethane (500 mL). The resulting crude product was purified by silica gel column chromatography using hexane-ethyl acetate as an elution solvent to obtain a target 3'-protected thymidine 9 (13 g, yield: 88%).

Step 9: Synthesis of $T_{p(OCH2CH=CH2)}T_{OTBS}$ (10)

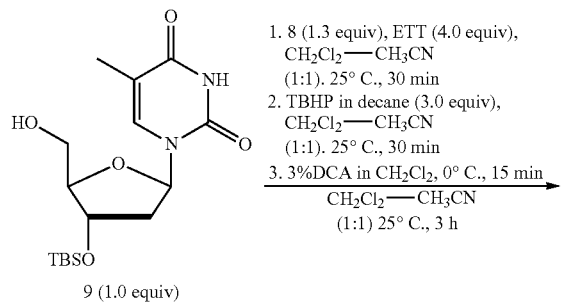

[Chemical Formula 18]

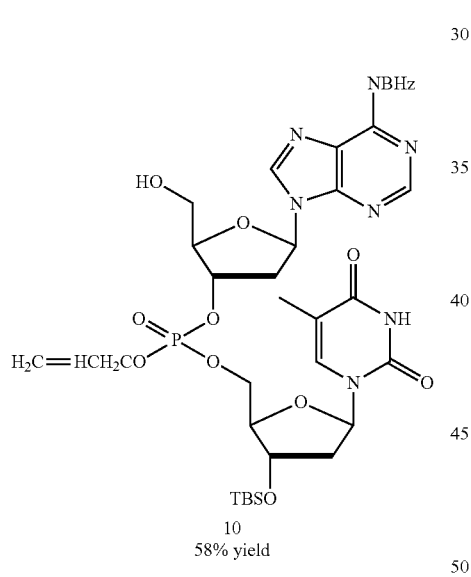

To a dichloromethane-acetonitrile (1:1, 10 mL) solution of phosphoramidite monomer 8 (1.3 g, 1.0 mmol) and 3'-protected thymidine 9 (0.36 g, 1.0 mmol), 5-ethylthio-1H-tetrazole (0.62 g, 4.0 mmol) was added. After stirring at room temperature for 30 minutes, a decane solution of TBHP (tert-butyl hydroperoxide) (0.60 mL, 3.0 mmol) was added, and the mixture was further stirred at room temperature for 30 minutes. After concentrating the reaction solution, the resulting crude product was treated with a dichloromethane solution (20 mL) of 3% dichloroacetic acid at room temperature for 15 minutes, and then the reaction solution was purified by silica gel column chromatography using dichloromethane-methanol as an elution solvent to obtain a target 5'-unprotected dAT dimer 10 (0.65 g, yield: 58%). {0060}

(Step 10: Synthesis of DMTr-$A^{Bz}_{p(OCH2CH=CH2)}A^{Bz}_{p(OCH2CH=CH2)}T_{OTBS}$ (11)

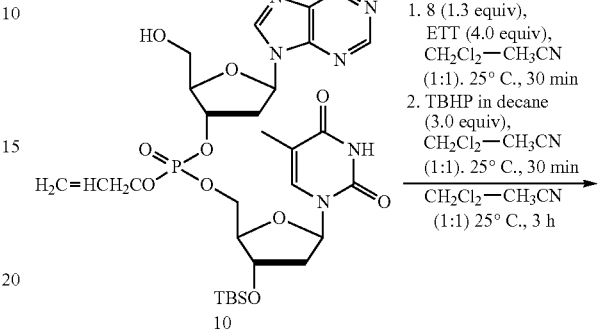

[Chemical Formula 19]

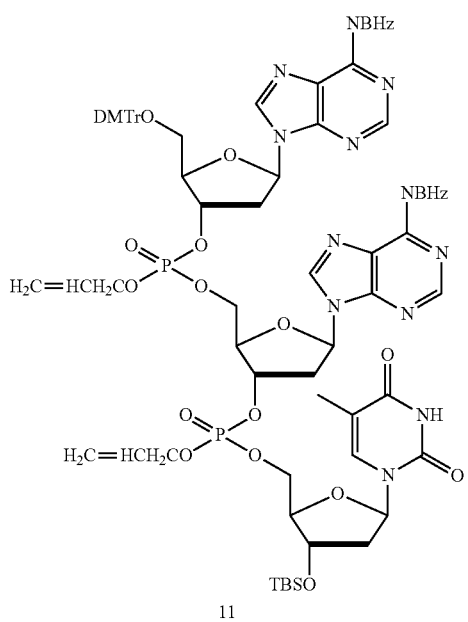

To a dichloromethane-acetonitrile solution (10 mL) of phosphoramidite monomer 8 (0.83 g, 0.99 mmol) and 5'-unprotected dAT dimer 10 (0.62 g, 0.76 mmol), 5-ethylthio-1H-tetrazole (0.47 g, 3.0 mmol) was added. After stirring at room temperature for 30 minutes, a decane solution of TBHP (0.46 mL, 2.3 mmol) was added thereto, and the mixture was further stirred at room temperature for 30 minutes. After concentration of the reaction solution, the resulting crude product was purified by silica gel column chromatography using dichloromethane-methanol as an elution solvent to obtain a target 5'-DMTr-dAAT trimer 11 (0.65 g, yield: 58%).

Step 11: Synthesis of DMTr-$A^{Bz}{}_{p(OCH2CH=CH2)}A^{Bz}{}_{p(OCH2CH=CH2)}T_{(OCH2CH=CH2)\,(N(i-C3H7)2)}$ (12)

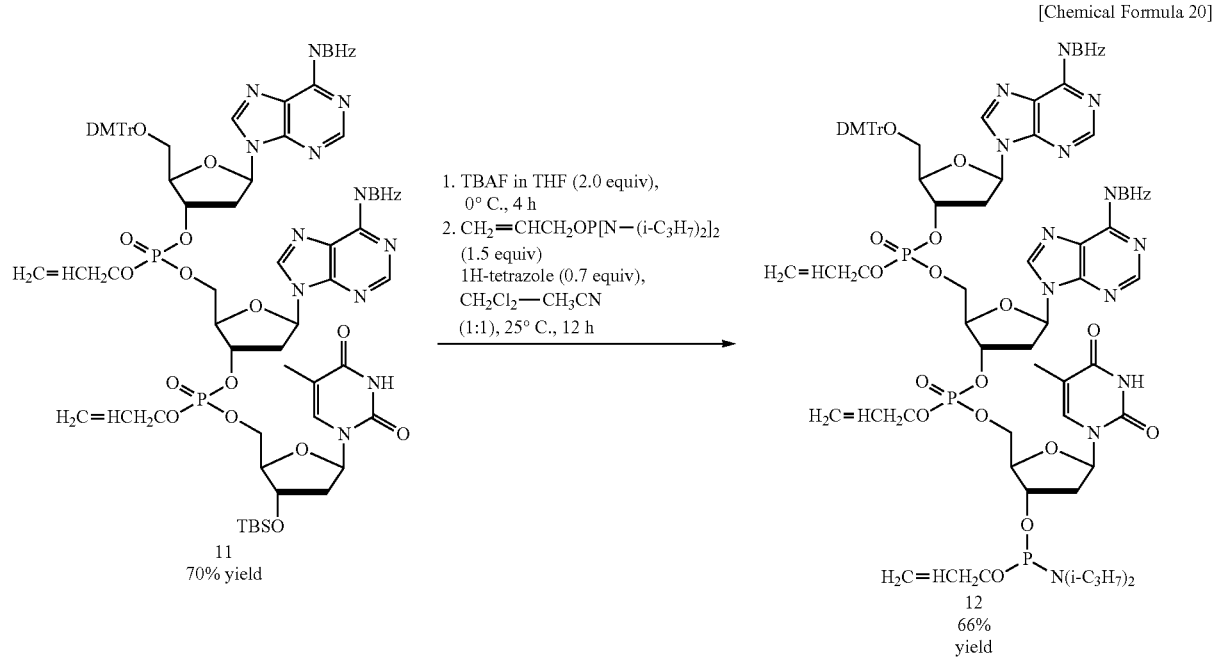

[Chemical Formula 20]

To 5'-DMTr-dAAT trimer 11 (0.94 g, 0.60 mmol), a THF solution of tetrabutylammonium fluoride (1.2 mL, 1.2 mmol) was added at 0° C. After stirring for 4 hours, the reaction solution was concentrated, and the resulting crude product was purified by silica gel column chromatography using dichloromethane-methanol as an elution solvent and dried under vacuum overnight. A portion of this intermediate (0.71 g, 0.49 mmol) was used to make a dichloromethane-acetonitrile solution (5.0 mL), and then a phosphitylating agent $CH_2=CHCH_2OP[N(i-C_3H_7)_2]_2$ (0.21 mL, 0.74 mmol) and 1H-tetrazole (0.024 g, 0.34 mmol) were added thereto in two parts at 0° C. After stirring the mixture at room temperature for 12 hours, dichloromethane (5.0 mL) was added thereto, and purification was performed by silica gel column chromatography using hexane-ethyl acetate as an elution solvent to obtain a target 5'-DMTr protected trimer phosphoramidite 12 (0.39 g, overall yield: 66%).

Step 12: Synthesis of DMTr-A$^{Bz}_{p(OCH2CH=CH2)}$A$^{Bz}_{p(OCH2CH=CH2)}$A$^{Bz}_{p\ (OCH2CH=CH2)}$T$_{OTBS}$ (13)

Step 13: Synthesis of DMTr-A$^{Bz}_{p(OCH2CH=CH2)}$A$^{Bz}_{p(OCH2CH=CH2)}$A$^{Bz}_{p\ (OCH2CH=CH2)}$T$_{OH}$ (14)

[Chemical Formula 21]

[Chemical Formula 22]

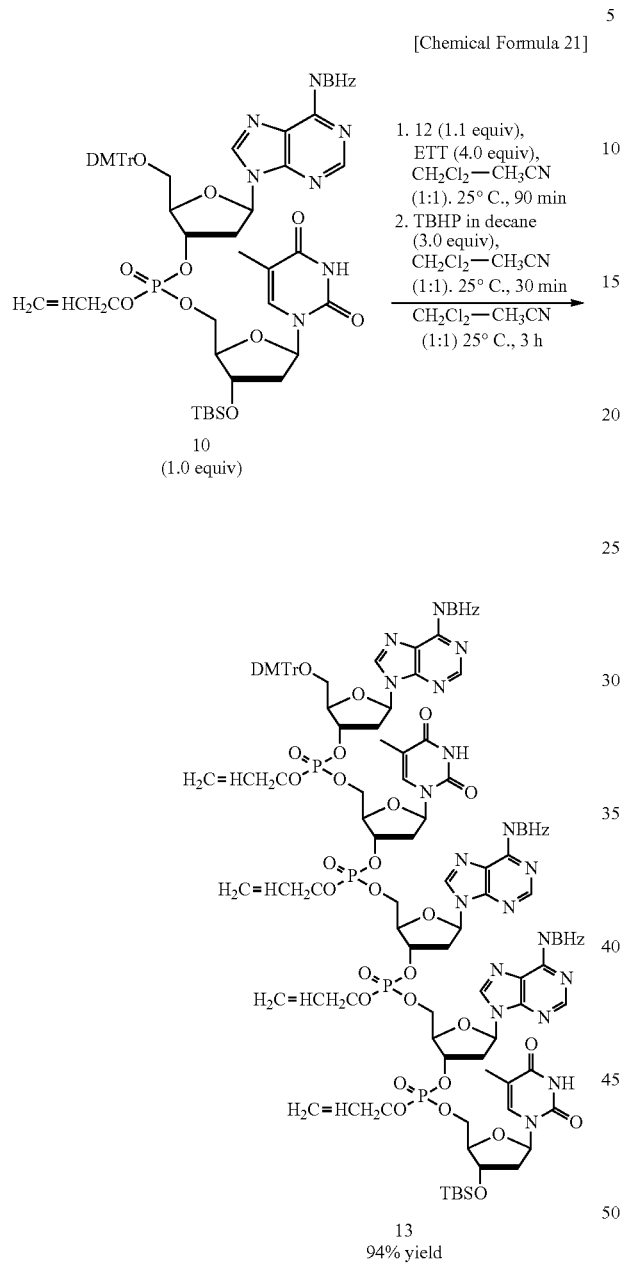

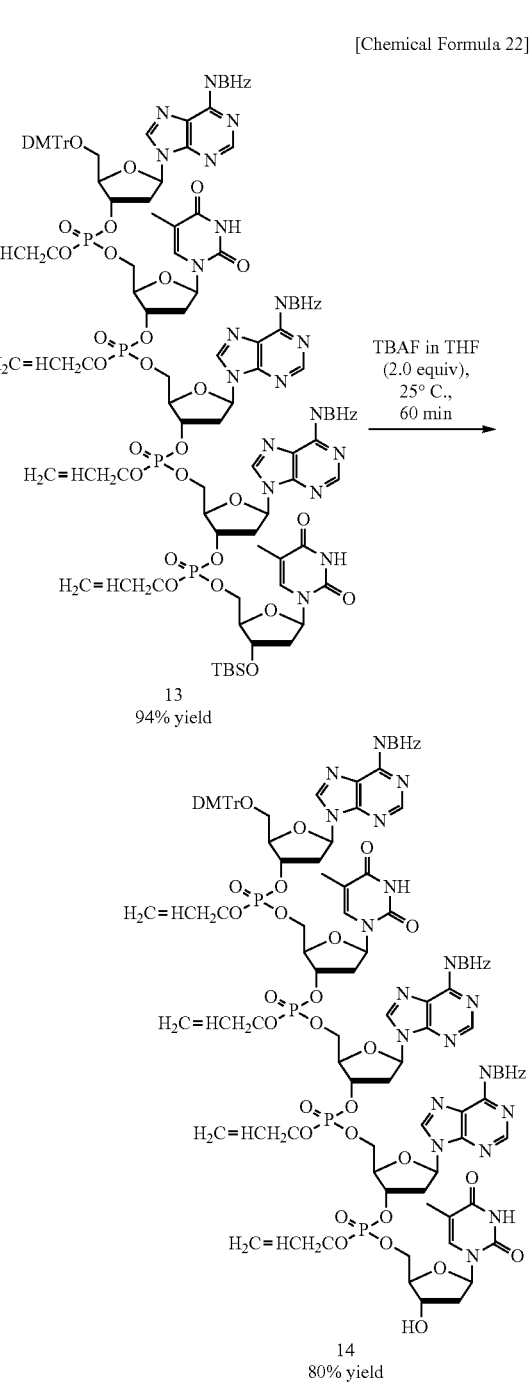

To a dichloromethane-acetonitrile solution (6 mL) of 5'-DMTr protected trimer phosphoramidite 12 (0.54 g, 0.33 mmol) and 5'-unprotected dimer 10 (0.24 g, 0.30 mmol), 5-ethylthio-1H-tetrazole (0.19 g, 1.2 mmol) was added. After stirring at room temperature for 90 minutes, a decane solution of TBHP (0.20 mL, 0.9 mmol) was added thereto, and the mixture was further stirred at room temperature for 30 minutes. After concentration of the reaction solution, the resulting crude product was purified by silica gel column chromatography using dichloromethane-methanol as an elution solvent to obtain a target 5', 3'-protected dAATAT pentamer 13 (0.67 g, yield: 94%).

To a 5', 3'-protected dAATAT pentamer 13 (0.67 g, 0.28 mmol), a THF solution of tetrabutylammonium fluoride (0.56 mL, 0.56 mmol) was added at 0° C. After stirring for 4 hours, the reaction solution was concentrated, and the resulting crude product was purified by silica gel column chromatography using dichloromethane-methanol as an elution solvent to obtain a target 5'-protected, 3'-unprotected pentamer 14 (0.51 g, overall yield: 80%).

Step 14: Synthesis of DMTr-A$^{Bz}_{p(OCH2CH=CH2)}$A$^{Bz}_{p(OCH2CH=CH2)}$A$^{Bz}_{p(OCH2CH=CH2)}$T$_{(OCH2CH=CH2)\,(N(i-C3H7)2)}$ (15)

[Chemical Formula 23]

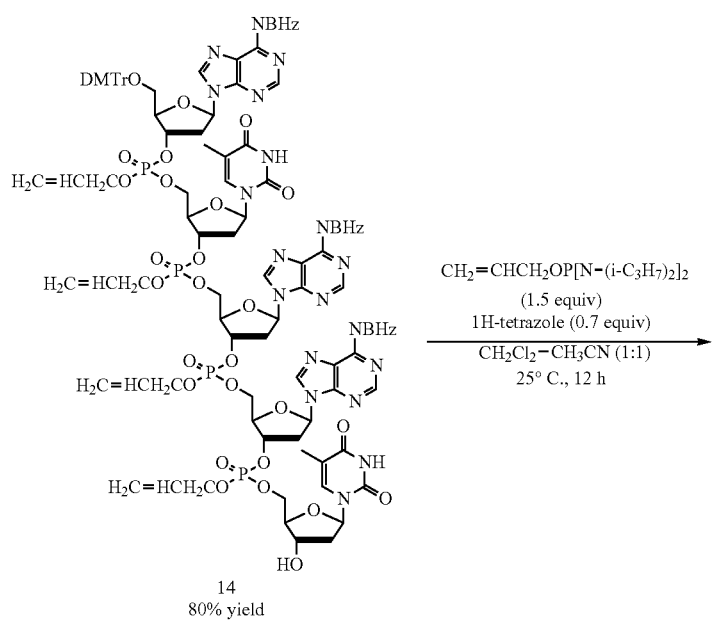

14
80% yield

CH$_2$=CHCH$_2$OP[N−(i-C$_3$H$_7$)$_2$]$_2$
(1.5 equiv)
1H-tetrazole (0.7 equiv)
―――――――――――
CH$_2$Cl$_2$−CH$_3$CN (1:1)
25° C., 12 h

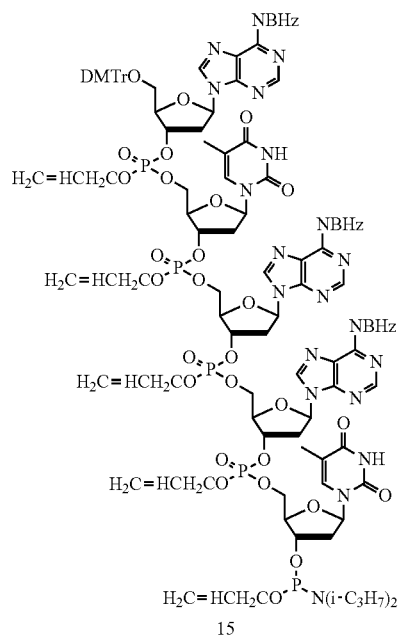

15

To a dichloromethane-acetonitrile solution (2.0 mL) of 5'-protected, 3'-unprotected dAATAT pentamer 14 (0.46 g, 0.21 mmol), a phosphitylating agent CH$_2$=CHCH$_2$OP[N(i-C$_3$H$_7$)$_2$]$_2$ (0.89 μL, 0.31 mmol) and 1H-tetrazole (0.010 g, 0.14 mmol) were added in two parts at 0° C. After stirring at room temperature for 12 hours, dichloromethane (5.0 mL) was added, and purification was performed by silica gel column chromatography using hexane-ethyl acetate as an elution solvent to obtain a target pentamer phosphoramidite 15 (0.41 g, overall yield: 81%).

Example 4

Solid-Phase Synthesis of dT$_{18}$

Figure 3:
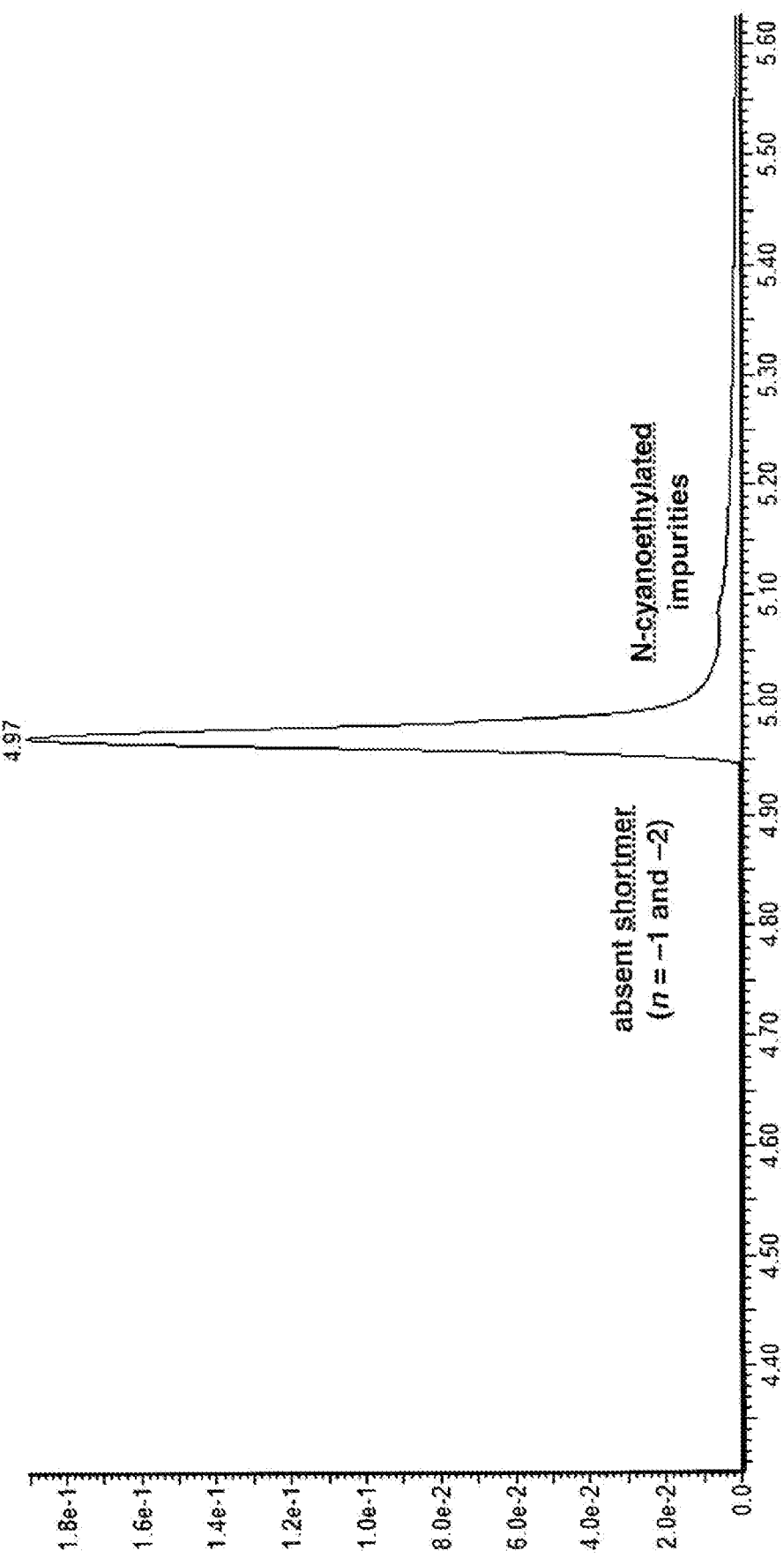
FIG. 3 is a chart showing an LC spectrum of an oligothymidine 18-mer synthesized using the segment for use in synthesis of an oligonucleotide obtained in Example 1.

In an M-2-MX oligonucleotide solid-phase synthesizer manufactured by NTS, using the synthetic segment (tetramer phosphoramidite) 3 obtained in Example 1, an oligonucleotide (dT 18-mer) was synthesized from universal linker CPG1000 A (1.0 μmol) manufactured by ChemGene as a starting substance by the following protocol.
Synthesis Cycle:
(Condensation)
  0.1 M tetramer phosphoramidite 3/acetonitrile solution (14.4 μL)
  0.25 M 5-benzylthiotetrazole/acetonitrile solution (24.8 μL)
  Reaction time: 2 minutes
(Capping)
  10% acetic anhydride/THF solution (320 μL)
  0.2 M N-methylimidazole/acetonitrile solution
  Reaction time: 1 minute
(Oxidation)
  0.05 M iodine/water/pyridine solution (320 μL)
(Detritylation)
  10% dichloroacetic acid/toluene solution (765 μL)
  Reaction time: 2 minutes
(Detaching/Deprotection)
  Concentrated aqueous ammonia
  Reaction time: 60 minutes, room temperature An LC spectrum of the resulting dT 18-mer is shown in FIG. 3.

From the above, according to the segment for use in synthesis of an oligonucleotide in the present embodiment, an amidite having a length of a nucleoside trimer or more may be used in synthesis of oligonucleotide. For this reason, in the case where an oligonucleotide having a target length equivalent to N-mer is synthesized, an (N-1)-mer which is shorter by one base, an (N-2)-mer which is shorter by two bases, etc., generated in the coupling step of monomer amidite in general-purpose synthesis of oligonucleotides, are not generated. As a result, in purifying the N-mer using chromatography or the like in the final stage of synthesis of an oligonucleotide, the difference in mobility between the target N-mer and the by-products having a length equivalent to (N-3)-mer or less is large, so that the purification burden for separating the N-mer and others can be reduced.

Also, the segment for use in synthesis of an oligonucleotide in the present embodiment enables to reduce the number of steps required for synthesizing the same N-mer oligonucleotide in comparison with the conventional method of extending one base each at a time. The yield of the oligonucleotide having a target length can be therefore improved.

Also, in production of the segment for use in synthesis of an oligonucleotide in the present embodiment, a phosphate bond moiety partially oxidized/sulfurized can be formed at the segment stage. Accordingly, even in the case where only a part of the phosphate bonds in an oligonucleotide is made into an oxidized/sulfurized state different from the phosphate bonds in other parts, an oligonucleotide containing a target modified phosphate bond moiety can be synthesized more easily without changing the synthesis procedure of the oligonucleotide.

Further, in the method for producing a segment for use in synthesis of an oligonucleotide of the present embodiment, a nucleoside having 5'-hydroxyl group only protected, or a nucleoside having both of 5'-hydroxyl group and 3'-hydroxyl group unprotected, is directly reacted with a phosphitylating agent for amidite preparation. Accordingly, it is not necessary to purchase a commercially available 3'-amidite monomer or prepare the monomer in advance. Therefore, a larger amount of a target segment for use in synthesis of an oligonucleotide can be produced as compared with the conventional method.

Further, the segment for use in synthesis of an oligonucleotide in the present embodiment may be used in the case where a large amount of oligonucleotide having a relatively short chain is synthesized by the liquid-phase synthesis method, and also in the case where an oligonucleotide having a long chain is synthesized by the solid-phase synthesis method. Since no by-products having a length of N-1 or N-2 are generated, the burden imposed by purification after synthesis of an N-mer oligonucleotide having a long chain in particular can be reduced, so that a target N-mer oligonucleotide can be obtained through a more convenient purification.

What is claimed is:

1. A segment for use in synthesis of an oligonucleotide, represented by the following formula (I):

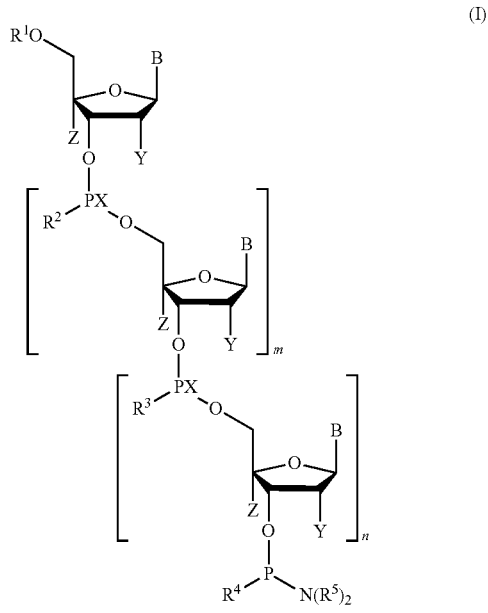

wherein B is independently a nucleoside base unprotected or protected with a protecting group;

$R^1$ is a protecting group;

$R^2$, $R^3$ and $R^4$ are independently $OCH_2CH_2CN$, $SCH_2CH_2CN$, $OCH_2CH=CH_2$, or $OCH_3$;

$R^5$ is a substituted or unsubstituted aliphatic group, or a substituted or unsubstituted aromatic group;

X is independently a lone pair, $=O$ or $=S$, at least one of X being a lone pair;

Y is independently H, $NHR^6$, a halogen, CN, $CF_3$ or a hydroxyl group protected with an acyl protecting group, an ether protecting group or a silyl protecting group;

$R^6$ is H, an aliphatic group or an aromatic group;

Z is independently H, an alkyl, an O-alkyl, an N-alkyl or a halogen, or forms a Z-Y bond with Y; and (m+n) is an integer of 3 or more and 23 or less.

2. The segment for use in synthesis of an oligonucleotide according to claim 1, wherein in the case where B in formula (I) is a nucleoside base protected with a protecting group, the protecting group is an acyl protecting group.

3. The segment for use in synthesis of an oligonucleotide according to claim 1, wherein in formula (I), $R^1$ is a protecting group removable under acidic conditions or a trialkylsilyl group;

Y is H or a hydroxyl group protected with a t-butyldimethylsilyl group;

Z is H; and $R^5$ is an isopropyl group.

4. A method for producing a segment for use in synthesis of an oligonucleotide, represented by the following formula (I):

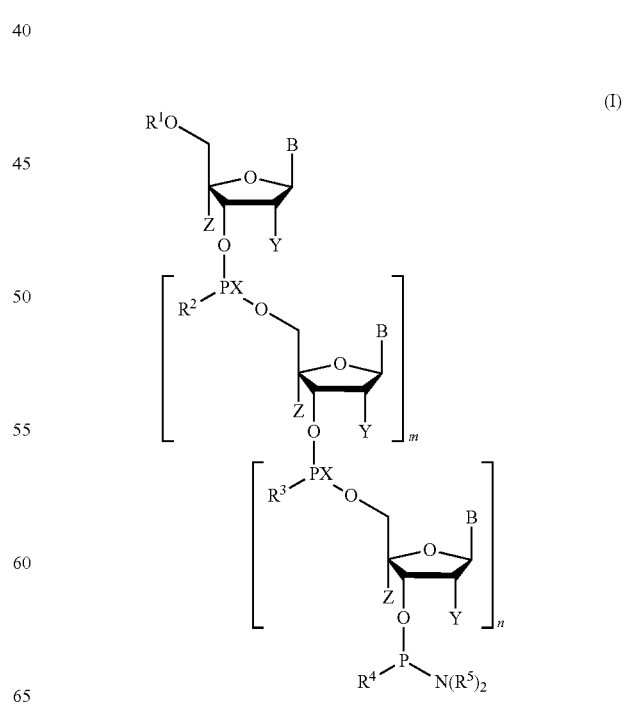

wherein B is independently a nucleoside base unprotected or protected with a protecting group;

$R^1$ is a protecting group;

$R^2$, $R^3$ and $R^4$ are independently $OCH_2CH_2CN$, $SCH_2CH_2CN$, $OCH_2CH=CH_2$, or $OCH_3$;

$R^5$ is a substituted or unsubstituted aliphatic group, or a substituted or unsubstituted aromatic group;

X is independently a lone pair, =O or =S;

Y is independently H, $NHR^6$, a halogen, CN, $CF_3$ or a hydroxyl group protected with an acyl protecting group, an ether protecting group or a silyl protecting group;

$R^6$ is H, an aliphatic group or an aromatic group;

Z is independently H, an alkyl, an O-alkyl, an N-alkyl or a halogen, or forms a Z-Y bond with Y; and (m+n) is an integer of 2 or more and 23 or less;

the method comprising:

(a) reacting a nucleoside represented by the following formula (II):

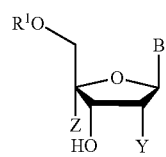

(II)

with a phosphitylating compound having a structure of $R^2P\{N(R^5)_2\}_2$ and a nucleoside having a structure of the following formula (III):

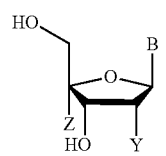

(III)

to prepare a compound having a structure of the following formula (IV):

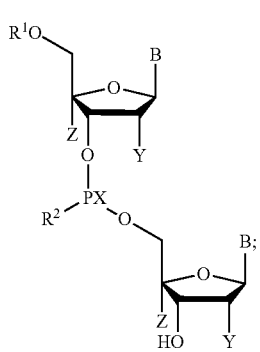

(IV)

(b) reacting the compound having a structure of formula (IV) with a phosphitylating compound having a structure of $R^3P\{N(R^5)_2\}_2$ and a nucleoside having a structure of formula (III) or a compound having a structure of the following formula (V):

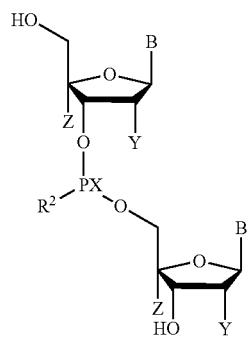

(V)

or a compound having a structure of the following formula (VI):

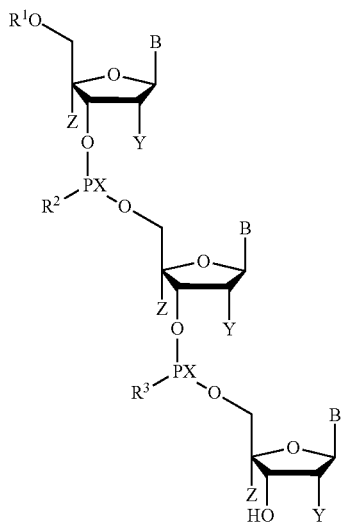

(VI)

to prepare a compound having a structure of the following formula (VII):

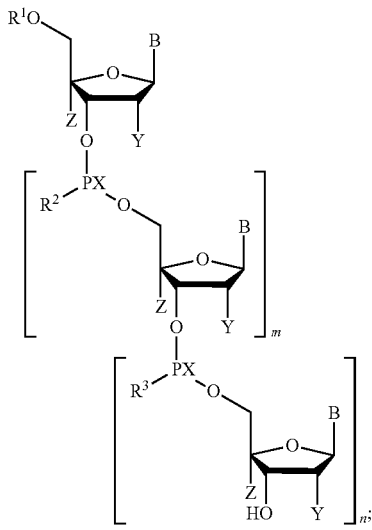

(VII)

(c) repeating (b) at least one time on an as needed basis; and
(d) reacting the resulting intermediate with a phosphitylating compound having a structure of $R^4P\{N(R^5)_2\}_2$ to prepare a segment having a structure of formula (I).

5. The method according to claim 4, wherein in the case where B in formula (I) is a nucleoside protected with a protecting group, the protecting group is an acyl protecting group.

6. The method according to claim 4, wherein in formula (I),
$R^1$ is a protecting group removable under acidic conditions;
Y is H or a hydroxyl group protected with a t-butyldimethylsilyl group;
Z is H, and
$R^5$ is an isopropyl group.

7. The method according to claim 4, further comprising reacting the compound represented by formula (IV) obtained in (a) or the compound represented by formula (VII) obtained in (b) with an oxidizing agent or sulfurizing agent on an as needed basis.

8. A method for synthesizing an oligonucleotide using the segment for use in synthesis of an oligonucleotide, represented by formula (I) according to claim 1, the method comprising:
(a) condensing an amidite moiety of the segment for use in synthesis of an oligonucleotide represented by formula (I) with a hydroxyl group of a nucleoside or nucleotide;
(b) oxidizing or sulfurizing a phosphite-linkage position obtained in (a); and
(c) deprotecting the terminal protecting group of the segment for use in synthesis of an oligonucleotide condensed with a nucleoside or nucleotide in (a).

9. The method according to claim 8, wherein each of (a), (b) and (c) is performed in a solution.

10. The method according to claim 8, wherein each of (a), (b) and (c) is performed on a solid-support.

* * * * *